United States Patent [19]
Dominianni et al.

[11] Patent Number: 6,121,282
[45] Date of Patent: Sep. 19, 2000

[54] HYPOGLYCEMIC AND HYPOLIPIDEMIC COMPOUNDS

[75] Inventors: Samuel James Dominianni; William Harlan Gritton, both of Indianapolis, Ind.

[73] Assignee: Eli Lilly and Company, Indianapolis, Ind.

[21] Appl. No.: 09/216,470

[22] Filed: Dec. 18, 1998

Related U.S. Application Data

[63] Continuation of application No. PCT/US97/11514, Jun. 30, 1997.
[60] Provisional application No. 60/021,017, Jul. 1, 1996.

[51] Int. Cl.$^7$ ............... C07D 217/16; A61K 31/47
[52] U.S. Cl. ............................. 514/307; 546/147
[58] Field of Search ............... 546/147; 374/307

[56] References Cited

U.S. PATENT DOCUMENTS

| | | | |
|---|---|---|---|
| 4,902,695 | 2/1990 | Ornstein | 514/307 |
| 4,988,720 | 1/1991 | Cawthorne et al. | 514/377 |
| 5,036,079 | 7/1991 | Clark et al. | 514/333 |
| 5,236,934 | 8/1993 | VanAtten | 514/307 |
| 5,246,943 | 9/1993 | Blankley et al. | 514/307 |
| 5,306,726 | 4/1994 | Hulin | 514/375 |
| 5,350,757 | 9/1994 | Blankley et al. | 514/307 |
| 5,489,686 | 2/1996 | Blankley et al. | 546/147 |
| 5,525,614 | 6/1996 | Blankley et al. | 514/307 |
| 5,616,819 | 4/1997 | Boyce et al. | 570/167 |

FOREIGN PATENT DOCUMENTS

| | | |
|---|---|---|
| 0 345 747 A2 | 12/1989 | European Pat. Off. . |
| 0 421 436 | 4/1991 | European Pat. Off. . |
| 0 764 652 | 3/1997 | European Pat. Off. . |
| WO 92/21342 | 12/1992 | WIPO . |
| WO 95/09001 | 4/1995 | WIPO . |
| WO 96/00736 | 1/1996 | WIPO . |
| WO 97/10367 | 3/1997 | WIPO . |
| WO 93/23409 | 11/1998 | WIPO . |

OTHER PUBLICATIONS

J.E. Gerich in New Engl. J. Med., 321, 1231–1245 (1989).
Diabetes Care, 18, Supplement 1, 86–93 (1995).
Ellingboe, et al., J. Med. Chem. 36:2485–2493 (1993).
Sonntag, Chem. Rev. 52:258–294 (1953).
Ugi, et al, Agnew. Chem. Intern. Ed. Engl. 4:472–484 (1965); also Mar. pp. 777–778.
Bose, A.K., et al., J. Can. Chem., 62:2498 (1984).
Cantello, et al., J. Med. Chem, 37:3977–3985 (1994).
C.W. Still, et al., J. Org. Chem. 43:2923 (1989).
Letsinger, R.L. and Ogilvie, K.K.; J. Org. Chem. 32:296 (1967).
Kugel, C., Lellouche, J.–P. and Beaucourt, J.–P., Tetrahedron Lett. 30:4947 (1989).
Arrieta, A. and Palmo, C., Synthesis (1982) 1050.
J. Med. Chem. 35:2617 (1992).

*Primary Examiner*—Zinna Northington Davis
*Attorney, Agent, or Firm*—Paul R. Darkes; Francis O. Ginah; James J. Kelley

[57] ABSTRACT

This invention provides 1,2,3,4-tetrahydroisoquinoline compounds and their pharmaceuticallyacceptable salts, pharmaceutical formulations of said compounds, and methods for treating hyperglycemia associated with non-insulin dependent diabetes and for treating hyperlipidemia.

17 Claims, No Drawings

HYPOGLYCEMIC AND HYPOLIPIDEMIC COMPOUNDS

This application claims the benefit of PCT Application No. PCT/US97/11514, filed Jun. 30, 1997, which in turn, claims the benefit of Provisional Application No. 60/021,017, filed Jul. 1, 1996.

This invention relates to the treatment and control of hyperglycemia, such as occurs in non-insulin-dependent diabetes mellitus (NIDDM). This invention also relates to treatment and control of hyperlipidemia.

BACKGROUND OF THE INVENTION

The disease, diabetes mellitus, is recognized in two forms. Type I diabetes requires exogenous insulin for control of the disease because it appears that endogenous production of insulin by the Isles of Langerhans in the pancreas is extremely poor or non-existent. Type I diabetes is often referred to as insulin-dependent diabetes mellitus (IDDM). Type II, non-insulin-dependent diabetes mellitus (NIDDM), is characterized by defects of insulin sensitivity in peripheral tissues such as adipose tissue and muscle, as described by J. E. Gerich in *New Engl. J. Med.*, 321, 1231–1245 (1989).

Hyperlipidemia is often observed in diabetics (*Diabetes Care*, 18, Supplement 1, 86–93, 1995). The combination of hyperlipidemia and hyperglycemia greatly increases the risk of cardiovascular diseases in diabetics. Successful treatment of hyperlipidemia and hyperglycemia in diabetics is needed urgently.

Blank reviewed hypoglycemic agents (*Burger's Medicinal Chemistry*, 4th Ed., Part II, John Wiley and Sons, N.Y., 1979, 1057–1080). Newer hypoglycemic agents were reviewed by Hulin in Progress in *Medicinal Chemistry*, 31, ed. G. P. Ellis and D. K. Luscombe, Elsevier Publishing Co., 1993.

Currently, partial control of NIDDM is achieved by a diet and exercise regimen, by administration of exogenous insulin, by administration of hypoglycemic agents, (e.g. the sulfonylureas), or by some combination of these protocols. Sulfonylureas, such as chloropropamide, acetohexamide and tolbutamide, are useful orally-effective hypoglycemic agents achieving success in the control of NIDDM in numbers of patients. However, drugs currently available for the control of the hyperglycemia associated with type II diabetes mellitus (NIDDM) possess significant liabilities or limitations of efficacy. (Ellingboe, et al., *J. Med. Chem.* 36:2485–2493, 1993). Considerable effort has been expended toward developing novel, orally-administered antihyperglycemic drugs. A preferred therapeutic approach for treating NIDDM incorporates drugs that counteract insulin resistance rather than those that stimulate endogenous insulin secretion. (J. R. Colca and D. R. Morton, *New Antidiabetic Drugs*, ed. C. J. Bailey and P. R. Flatt, Smith-Gordon and Company, Ltd., London, Chapter 24, 1990). Drugs that treat insulin resistance are called insulin sensitivity enhancers.

Sato, Y, et al. (*Diabetes Research and Clinical Practice*, 12:53–60, 1991) described the hypoglycemic effect of D-phenylalanine derivatives. In normal dogs, the hypoglycemic activity of the compound was greater than that of tolbutamide but less than that of glibenclamide. The compounds exerted a rapid hypoglycemic effect and improved glucose tolerance in genetically diabetic KK mice and in streptozotocin-treated rats. Yamasaki, et al. disclosed a group of 2-quinolone derivatives showing antidiabetic activity in NIDDM (WO 92/21342).

Some known hypoglycemic compounds also reduce serum cholesterol or triglyceride levels. (Clark, et al., U.S. Pat. No. 5,036,079). The combination of these biological activities in one compound is particularly advantageous because diabetics are highly susceptible to hyperlipidemia. Hulin, in U.S. Pat. No. 5,306,726, claimed phenylpropionic acid derivatives and disclosed compounds that had hypoglycemic and hypocholesterolemic activity useful for the treatment of diabetes and atherosclerosis. Miyata, et al. found a class of phosphonic diester derivatives useful for treating diabetes and hyperlipidemia (WO 93/23409). Hypolipidemic amino acid derivatives were disclosed in JA-028189.

SUMMARY OF THE INVENTION

This invention provides 1,2,3,4-tetrahydroisoquinoline compounds of the Formula I:

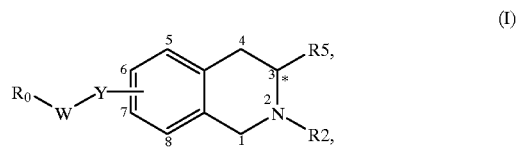

(I)

wherein:
$R^0$ is selected from the group consisting of

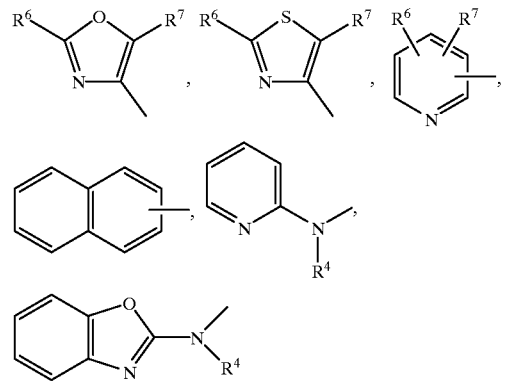

and
$R^2$ is hydrogen, $C_{1-4}$ acyl, $C_{1-4}$ alkyloxycarbonyl, $C_{1-4}$ alkylaminocarbonyl, arylcarbonyl, aryloxycarbonyl, aryloxy $C_{1-4}$ alkylcarbonyl, arylaminocarbonyl, aryl $C_{1-4}$ acyl, aryl $C_{1-4}$ alkyloxycarbonyl, aryl $C_{1-4}$ alkylaminocarbonyl, aryl $C_{1-4}$ alkylsulfonyl, or an amino-protecting group;
$R^4$ is hydrogen, or $C_{1-4}$ alkyl;
$R^5$ is —COOH, —CONR$^{10}$R$^{11}$, —CN, —CONHOH, or

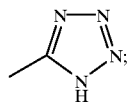

$R^6$ is hydrogen, $C_{1-4}$ alkyl, aryl, or aryl $C_{1-4}$ alkyl;
$R^7$ is hydrogen, halogen, or $C_{1-4}$ alkyl;
$R^9$ is hydrogen, $C_{1-4}$ alkyl, or aryl;
$R^{10}$ and $R^{11}$ are independently hydrogen, $C_{1-4}$ alkyl, or aryl;
W is —(CH$_2$)n—;
Y is attached at position 6 or at position 7 of the 1,2,3,4-tetrahydroisoquinoline moiety, and is —O—, —S—, —SO—, —SO$_2$—, —NH—, —CONR$^9$—, —NR$^9$—SO$_2$—, or —SO$_2$—NR$^9$—; and n is 1 to 4;

or a pharmaceutically-acceptable salt thereof.

This invention also provides pharmaceutical formulations of the compounds of Formula I, and methods for treating hyperglycemia associated with non-insulin dependent diabetes and for treating hyperlipidemia by administering to a mammal an effective dose of a compound of the Formula I.

DETAILED DESCRIPTION

A "mammal" is an individual animal that is a member of the taxonomic class Mammalia. The class Mammalia includes humans, monkeys, chimpanzees, gorillas, cattle, swine, horses, sheep, dogs, cats, mice, and rats.

"1,2,3,4-Tetrahydroisoquinoline" refers to a compound of the general structure

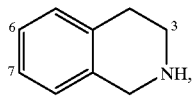

where the numerals designate positions of particular relevance to the present invention.

"Halogen" refers to fluoro, chloro, bromo or iodo.

"$C_{1-3}$ alkyl" includes methyl, ethyl, n-propyl, and isopropyl.

"$C_{1-4}$ alkyl" refers to straight or branched alkyl radicals having 1 to 4 carbon atoms, for example, methyl, ethyl, n-propyl, iso-propyl, n-butyl, sec-butyl, and t-butyl.

"$C_{1-4}$ alkoxy" refers to radicals having 1 to 4 carbon atom alkyl chains, straight or branched, bonded to an oxygen atom, for example, methoxy, ethoxy, n-propoxy, iso-propoxy, t-butoxy, and the like.

"$C_{1-4}$ acyl" refers to radicals of the formula

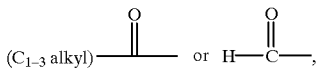

and includes, for example, formyl, acetyl, propionyl, and the like.

"$C_{1-4}$ alkyloxycarbonyl" refers to radicals of the form

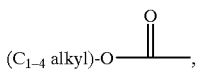

for example, methoxycarbonyl, ethoxycarbonyl, and the like.

"$C_{1-4}$ alkylaminocarbonyl" refers to radicals of the form

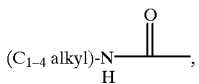

for example, methylaminocarbonyl, ethylaminocarbonyl, 2-propylaminocarbonyl, and the like.

"Aryl" refers to a substituted or unsubstituted aromatic radical selected from the group consisting of 2-furyl, 3-furyl, 2-thienyl 3-thienyl, 1-pyrrolyl, 2-pyrrolyl, 3-pyrrolyl, phenyl, 2-pyridyl, 3-pyridyl, 4-pyridyl, 1-naphthyl, 2-naphthyl, 2-benzofuryl, 3-benzofuryl, 4-benzofuryl, 5-benzofuryl, 6-benzofuryl, 7-benzofuryl, 2-benzothieny, 3-benzothieny, 4-benzothieny, 5-benzothieny, 6-benzothieny, 7-benzothienyl, 1-indolyl, 2-indolyl, 3-indolyl, 4-indolyl, 5-indolyl, 6-indolyl, 7-indolyl, and 8-indolyl. The optional substitutions of aryl may be at one or two carbon atoms of the aryl group, and may be with $C_{1-4}$ alkyl, $C_{1-4}$ alkoxy, halogen, —NO$_2$, —CN, —COOH, —CONH$_2$, —SO$_3$H, —SO$_2$NH$_2$ or trifluoromethyl. Examples of substituted aryl groups are 4-methyl-3-furyl, 3,4-dimethyl-2-thienyl, 2,4-dimethyl-3-thienyl, 3-ethoxy-4-methyl-2-benzofuryl, 2-cyano-3-benzofuryl, 4-trifluoromethyl-2-benzothienyl, 2-chloro-3-benzothienyl, 3,4-dichloro-2-pyridyl, 2-bromo-3-pyridyl, 2-fluoro-4-pyridyl, 4-fluoro-2-furyl, 2-carboxyphenyl, 4-carboxamidophenyl, 3-trifluoromethylphenyl, bromo-1-naphthyl, 2,3-dimethyl-1-naphthyl, 3-carboxy-2-naphthyl, 5-carboxy-8-chloro-1-naphthyl, 3-ethyl-2-furyl, 8-fluoro-2-naphthyl, 5-trifluoromethyl-2-naphthyl, 6-ethoxy-2-naphthyl, 6,7-dimethoxy-2-naphthyl, 3-carboxy-2-naphthyl, and the like.

"Arylcarbonyl" refers to radicals of the form

for example, phenylcarbonyl, 4-methyl-1-naphthylcarbonyl, 3-trifluoromethylphenylcarbonyl, and the like.

"Aryloxycarbonyl" refers to radicals of the form

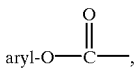

for example, phenyloxycarbonyl, 1-naphthyloxycarbonyl, 3-benzofuryloxycarbonyl, 2-benzothienyloxycarbonyl, 3-benzothienyloxycarbonyl, 2-pyridyloxycarbonyl, 3-pyridyloxycarbonyl, 3-ethyl-2-furyloxycarbonyl, 8-fluoro-2-naphthyloxycarbonyl, and the like.

"Arylaminocarbonyl", refers to radicals of the form

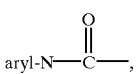

for example, phenylaminocarbonyl, 2-naphthylaminocarbonyl, 4-methyl-3-furylaminocarbonyl, 3,4-dimethyl-2-thienylaminocarbonyl, 2,4-dimethyl-3-thienylaminocarbonyl, 3-ethoxy-4-methyl-2-benzofurylaminocarbonyl, 2-cyano-3-benzofurylaminocarbonyl, 4-trifluoromethyl-2-benzothienylaminocarbonyl, 2-chloro-3-benzothienylaminocarbonyl, 3,4-dichloro-2-pyridylaminocarbonyl, 2-bromo-3-pyridylaminocarbonyl, 3-furylaminocarbonyl, 2-benzofurylaminocarbonyl, 4-pyridylaminocarbonyl, and the like.

"Aryl $C_{1-4}$ acyl" refers to radicals of the form

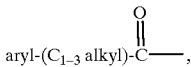

for example, para-trifluoromethylbenzylcarbonyl, phenylacetyl, 2-(1-naphthyl)ethylcarbonyl, 2-phenylethylcarbonyl, 2-(3-benzofuryl)ethylcarbonyl, 2-furylacetyl, and the like.

"Aryl $C_{1-4}$ alkyloxycarbonyl" refers to radicals of the form

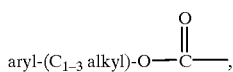

for example, benzyloxycarbonyl, 2-(2-naphthyl) ethoxycarbonyl, 6-phenylpropoxycarbonyl, 2-benzofurylmethoxycarbonyl, 3-chloro-4-methylbenzyloxycarbonyl, 4-carboxamidobenzyloxycarbonyl, and the like.

"Aryl $C_{1-4}$ alkylaminocarbonyl" refers to radicals of the form

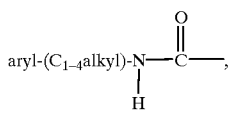

for example, phenylmethylaminocarbonyl, 2-(2-benzothienyl) propylaminocarbonyl, (2-naphthyl) methylaminocarbonyl, 2-thienylmethylaminocarbonyl, and the like.

"Aryl $C_{1-4}$ alkylsufonyl" refers to radicals of the form

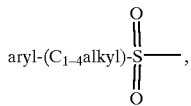

for example, phenylmethylsulfonyl, and the like.

"Aryl $C_{1-4}$ alkyl" refers to radicals of the form aryl—($C_{1-4}$ alkyl)—, for example, phenylmethyl, 2-(2-theinyl)ethyl, 3-(2-benzofuryl)propyl, benzyl, 4-chlorobenzyl, 3-ethyl-4-methylbenzyl, 3-chloro-4-methylbenzyl, 3,4-dichlorobenzyl, 3-isopropoxybenzyl, and the like.

The term "amino protecting group" as used herein refers to substituents of the amino group commonly employed to block or protect the amino functionality while reacting other functional groups on the compound. Examples of such amino-protecting groups include the formyl group, the phtalimido group, the trichloroacetyl group, the chloroacetyl, bromoacetyl, and iodoacetyl groups, urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, 2-(4-xenyl)isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)prop-2-yloxycarbonyl, cyclopentanyloxycarbonyl, 1-methylcylcopentanyloxycarbonyl, cyclohexanyloxycarbonyl, 1-methylcyclohexanyloxycarbonyl, 2-methylcyclohexanyloxycarbonyl, 2-(4-toluylsulfonyl) ethoxycarbonyl, 2-(methylsulfonyl)ethoxycarbonyl, 2-(triphenylphosphino)ethoxycarbonyl, 9-fluorenylmethoxycarbonyl ("FMOC"), 2-(trimethylsilyl) ethoxycarbonyl, allyloxycarbonyl, 1-(trimethylsilylmethyl) prop-1-en-3-yloxycarbonyl, 5-benzisoxalylmethoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy) benzyloxycarbonyl, isobornyloxycarbonyl, 1-piperidyloxycarbonyl, and the like; the benzoylmethylsulfonyl, the 2-(nitro)phenylsulfenyl group, the diphenylphosphine oxide group, and like amino protecting groups. The species of amino protecting group employed is not critical so long as the derivitized amino group is stable to the condition of subsequent reaction(s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by J. S. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and Sons, New York, N.Y., 1981, Chapter 7. The related term "protected amino" defines an amino group substituted with an amino protecting group discussed above.

The term "carboxy protecting group" as used herein refers to one of the ester derivatives of the carboxylic acid group commonly employed to block or protect the carboxylic acid group while reactions are carried out on other functional groups of the compound. Examples of such carboxylic acid protecting groups include benzyl, 4-nitrobenzyl, 4-methoxybenzyl, 3,4-dimethoxybenzyl, 2,4-dimethoxybenzyl, 2,4,6-trimethoxybenzyl, pentamethylbenzyl, 3,4-methylenediozybenzyl, benzyhydryl, 4,4'-dimethoxybenzhydryl, 2,2,4,4'-tetramethoxybenzhydryl, t-butyl, isobutyl, n-butyl, propyl, isopropyl, ethyl, methyl, t-amyl, trityl, 4-methoxytrityl, 4,4'-dimethoxytrityl, 4,4',4"-trimethoxytrityl, trimethylsilyl, t-butyldimethylsilyl, phenyacyl, 2,2,2-trichloroethyl, B-(trimethylsilyl)ethyl, B-(di(n-butyl)methylsilyl)ethyl, p-toluenesulfonylethyl, 4-nitrobenzylsulfonylethyl, allyl, cinnamyl, 1-(trimethylsilylmethyl)prop-1-en-3-yl, and like moieties. The species of carboxy-protecting group employed is not critical so long as the derivitized carboxylic acid is stable to the conditions of subsequent reaction(s) on other positions of the molecule and can be removed at the appropriate point without disrupting the remainder of the molecule. Carboxy protecting groups similar to those used in the cephalosporin, penicillin, and peptide arts can also be used to protect a carboxy group substituent of the compounds provided herein. Futher examples of these groups are found in E.Haslam, "Protective Groups in Organic Chemistry", J. G. W. McOmie, Ed., Plenum Press, New York, N.Y., 1981, Chapter 5 and T. W. Greene, "Protective Groups in Organic Synthesis", 2nd Ed., John Wiley and Sons, New York, N.Y., 1991, Chapter 5.

"Pharmaceutically-acceptable salt" refers to salts of the compounds of the Formula I which are substantially non-toxic to mammals. Typical pharmaceutically-acceptable salts include those salts prepared by reaction of the compounds of the present invention with a mineral or organic acid or an organic or inorganic base. Such salts are known as acid addition and base addition salts, respectively. It should be recognized that the particular counterion forming a part of any salt of this invention is not of a critical nature, so long as the salt as a whole is pharmaceutically-acceptable and as long as the counterion does not contribute undesired qualities to the salt as a whole.

Acids commonly employed to form acid addition salts are inorganic acids such as, without limitation, hydrochloric acid, hydrobromic acid, hydriodic acid, sulfuric acid, phosphoric acid, and the like, and organic acids, such as, without limitation, p-toluenesulfonic acid, methanesulfonic acid, oxalic acid, p-bromophenylsulfonic acid, carbonic acid, succinic acid, citric acid, benzoic acid, acetic acid, and the like.

Base addition salts include those derived from inorganic bases, such as, without limitation, ammonium hydroxide, alkaline metal hydroxides, alkaline earth metal hydroxides, carbonates, bicarbonates, and the like, and organic bases, such as, without limitation, ethanolamine, triethylamine, tris(hydroxymethyl)aminomethane, and the like. Examples of inorganic bases include, without limitation, sodium hydroxide, potassium hydroxide, potassium carbonate, sodium carbonate, sodium bicarbonate, potassium bicarbonate, calcium hydroxide, calcium carbonate, and the like.

Examples of such pharmaceutically-acceptable salts are, without limitation, the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like salts of the compound of Formula I. The preferred acid addition salts are those formed with mineral acids, such as, without limitation, hydrochloric acid, and hydrobromic acid, and those formed with organic acids, such as, without limitation, maleic acid and methanesulfonic acid. The potassium and sodium salt forms are particularly preferred base addition salts.

"Pharmaceutically-effective amount" means that amount of a compound that will elicit the biological or medical response of a tissue, system, or mammal that is being sought by a researcher or clinician.

The geometric property that is responsible for the non-identity of an object with its mirror image is called chirality. A compound that having a single chiral center may exist in either of two forms that are mirror images of each other. "Enantiomer" usually designates one of the two forms of such a compound. Enantiomer may also designate a homochiral collection molecules of a compound, or a heterochiral collection of molecules of a compound that contains an excess of one enantiomer over the other enantiomer. Absolute structural configuration of enantiomers of a chiral compound is designated by the letters "R" or "S", using the rules of R. S. Cahn, C. K. Ingold, and V. Prelog in *Agnew. Chem.*, 78:413 (1966); *Agnew. Chem. Int. Ed.*, 5:385 (1966). An equimolar mixture of two enantiomers whose physical state is unspecified is called a "racemate". The adjectival form is "racemic", as in "racemic substance." The term "racemate" includes within it "crystalline racemate", which may refer to a conglomerate, a racemic mixture, a racemic compound, or a pseudoracemate [J. Jacques, A. Collet, and S. H. Wilen, Enantiomers, Racemates, and Resolutions, Krieger Publ. Co., Malabar, Fla., 1991, pp. 4–5]. The asymmetric carbon atom at the position denoted by the star (*) creates the chirality of the compounds of Formula (I).

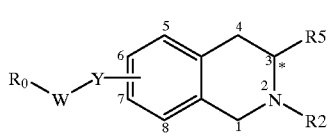

(I)

It will be understood that groups listed immediately below can be combined to create further, more narrowly limited groups of compounds. Preferred compounds of Formula I are those wherein:

$R^0$ is selected from the group consisting

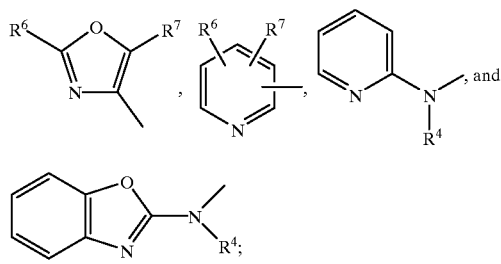

$R^0$ is

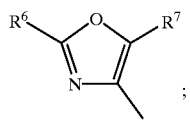

$R^0$ is

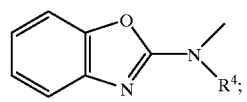

$R^0$ is

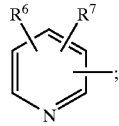

$R^0$ is

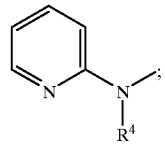

$R^0$ is

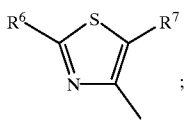

$R^2$ is arylcarbonyl, aryloxycarbonyl, arylaminocarbonyl, aryl $C_{1-4}$ alkyloxycarbonyl, aryloxy $C_{1-4}$ alkylcarbonyl, or aryl $C_{1-4}$ alkylsulfonyl;

$R^2$ is arylcarbonyl, aryloxycarbonyl, aryl $C_{1-4}$ alkyloxycarbonyl, aryloxy $C_{1-4}$ alkylcarbonyl, or aryl $C_{1-4}$ alkylsulfonyl;

$R^2$ is arylcarbonyl, aryloxycarbonyl, or aryl $C_{1-4}$ alkyloxycarbonyl;

$R^2$ is arylcarbonyl;

$R^2$ is aryloxycarbonyl $R^2$ is arylaminocarbonyl;

$R^2$ is aryl $C_{1-4}$ alkyloxycarbonyl;

$R^2$ is aryloxy $C_{1-4}$ alkylcarbonyl;

$R^2$ is aryl $C_{1-4}$ alkylsulfonyl;

$R^2$ is benzyloxycarbonyl, phenylcarbonyl, benzylcarbonyl, methylbenzylcarbonyl, phenyloxycarbonyl, para-chlorophenylcarbonyl, benzylsulfonyl, para-bromophenyloxycarbonyl, para-trifluoromethylphenyloxycarbonyl, para-methoxyphenyloxycarbonyl, para-n-butylphenyloxycarbonyl, or phenyloxymethylcarbonyl, benzylaminocarbonyl;

$R^4$ is hydrogen;

$R^4$ is methyl;

$R^5$ is —COOH;

$R^5$ is —CONR$^{10}$R$^{11}$;

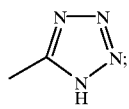

$R^5$ is $R^6$ is aryl;

$R^6$ is aryl $C_{1-4}$ alkyl;

$R^6$ is aryl methyl;

$R^6$ is phenyl;

$R^6$ is benzyl;

$R^7$ is hydrogen;

$R^7$ is halogen;

$R^7$ is $C_{1-4}$ alkyl;

$R^7$ is fluorine;

$R^7$ is methyl;

$R^9$ is hydrogen;

$R^9$ is $C_{1-4}$ alkyl;

$R^9$ is methyl;

$R^{10}$ and $R^{11}$ are independently hydrogen or $C_{1-4}$ alkyl;

$R^{10}$ and $R^{11}$ are both hydrogen;

$R^{10}$ and $R^{11}$ are independently $C_{1-4}$ alkyl;

W is —(CH$_2$)—;

W is —(CH$_2$)$_2$—;

W is —(CH$_2$)$_3$—;

W is —(CH$_2$)$_4$—;

Y is attached at position 7;

Y is attached at position 6;

y is —O—;

Y is —S—, —SO—, or —SO$_2$—;

Y is —S—;

Y is —CONR$^9$—, —NR$^9$—SO$_2$—, or —SO$_2$—NR$^9$—;

Y is —SO$_2$—, —NR$^9$—SO$_2$—, or —SO$_2$—NR$^9$—;

n is 1;

n is 2;

n is 3;

n is 4;

the compound is the R enantiomer;

the compound is the S enantiomer;

the compound is the racemate.

It likewise will be understood that the particularly preferred groups listed immediately below can be combined to create further, more narrowly limited groups of compounds. Particularly preferred compounds are those wherein:

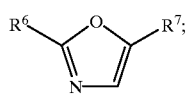

$R^0$ is $R^2$ is arylcarbonyl;

$R^2$ is aryloxycarbonyl;

$R^2$ is aryl $C_{1-4}$ alkyloxycarbonyl;

$R^2$ is benzyloxycarbonyl, phenylcarbonyl, benzylcarbonyl, methylbenzylcarbonyl, phenyloxycarbonyl, para-chlorophenylcarbonyl, benzylsulfonyl, para-bromophenyloxycarbonyl, para-trifluoromethylphenyloxycarbonyl, para-methoxyphenyloxycarbonyl, para-n-butylphenyloxycarbonyl, or phenyloxymethylcarbonyl, benzylaminocarbonyl;

$R^5$ is —COOH;

$R^6$ is aryl;

$R^6$ is phenyl;

$R^7$ is hydrogen;

W is —(CH$_2$)$_2$—;

Y is attached at position 6;

Y is attached at position 7;

Y is —O—;

Y is —S—;

n is 2 the compound is the R enantiomer;

the compound is the S enantiomer;

the compound is the racemate.

Further preferred compounds of Formula (I) are those wherein:

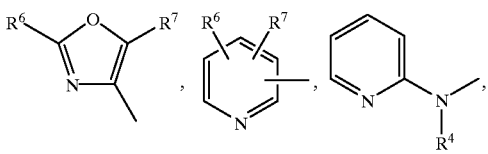

or

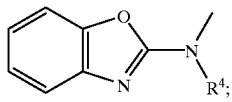

$R^2$ is hydrogen, $C_{1-4}$ alkyloxycarbonyl, arylcarbonyl, aryloxycarbonyl, arylaminocarbonyl, aryl $C_{1-4}$ alkyloxycarbonyl, aryloxy $C_{1-4}$ alkylcarbonyl, aryl $C_{1-4}$ alkylsulfonyl, or an amino-protecting group; $R^4$ is hydrogen or methyl;

$R^5$ is —COOH, —CONR$^9$R$^{10}$, or

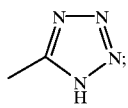

$R^6$ is aryl;
$R^7$ is hydrogen, halogen, or methyl;
$R^9$ and $R^{10}$ are hydrogen;
Y is —O— or —S—;
the compound is the R enantiomer;
the compound is the S enantiomer; and
the compound is the racemate.

More preferred compounds of Formula I are those wherein:

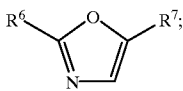

$R^0$ is
$R^2$ is arylcarbonyl, aryloxycarbonyl, aryl $C_{1-4}$ alkyloxycarbonyl, aryl $C_{1-4}$ alkylsulfonyl, or an amino-protecting group;
$R^5$ is —COOH;
$R^7$ is hydrogen, fluoro, or methyl;
Y is —O—; and
n is 1 or 2.

Particularly preferred compounds of Formula I are those wherein:

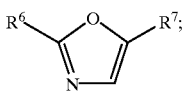

$R^0$ is
$R^2$ is hydrogen, benzyloxycarbonyl, phenylcarbonyl, benzylcarbonyl, methylbenzylcarbonyl, phenyloxycarbonyl, para-chlorophenylcarbonyl, benzylsulfonyl, para-bromophenyloxycarbonyl, para-trifluoromethylphenyloxycarbonyl, para-methoxyphenyloxycarbonyl, para-n-butylphenyloxycarbonyl, phenyloxymethylcarbonyl, benzylaminocarbonyl, or ethoxycarbonyl;

$R^6$ is phenyl;
$R^7$ is hydrogen;
Y is attached at the 6 position;
Y is attached at the 7 position; and
n is 2.

Preferred aryl radicals include phenyl, 1-naphthyl, and 2-naphthyl, optionally substituted with $C_{1-4}$ alkyl, $C_{1-4}$ alkoxy, halogen, —NO$_2$, or triflurormethyl. A more preferred aryl radical is phenyl, optionally substituted with $C_{1-4}$ alkyl, $C_{1-4}$ alkoxy, halogen, —NO$_2$, or triflurormethyl. A particularly preferred aryl radical is phenyl, optionally substituted at the para-position with methyl, ethyl, n-propyl, n-butyl, methoxy, fluoro, chloro, bromo, or trifluoromethyl.

A few compounds of this invention will be specifically mentioned to assure the reader's comprehension. This invention includes both racemates, and individual enantiomers.

7-[2-(2-phenyl-4-thiazolyl)ethoxy]-1,2,3,4-tetrahydro-N-benzyloxycarbonyl-isoquinoline-3-carboxylic acid;

7-[2-(2-phenyl-4-thiazolyl)ethoxy]-1,2,3,4-tetrahydro-N-benzyloxycarbonyl-isoquinoline-3-carboxylic acid, sodium salt;

7-[2-(2-phenyl-4-oxazolyl)ethoxy]-1,2,3,4-tetrahydro-N-benzylsulfonyl-isoquinoline-3-carboxylic acid, potassium salt;

7-[2-(5-ethyl-(2-naphthyl)-4-oxazolyl)ethoxy]-1,2,3,4-tetrahydro-N-para-chlorobenzyloxycarbonyl-isoquinoline-3-carboxylic acid;

7-[2-(5-methyl-2-phenyl-4-oxazolyl)ethoxy]-1,2,3,4-tetrahydro-N-benzyloxycarbonyl-isoquinoline-3-carboxylic acid, sodium salt;

7-[2-(2-phenyl-4-oxazolyl)ethoxy-1,2,3,4-tetrahydro-N-(3-chlorobenzoyl)-isoquinoline-3-carboxylic acid, calcium salt;

7-[2-(6-ethyoxy-2-pyridyl)ethoxy]-1,2,3,4-tetrahydro-N-ethoxycarbonyl-isoquinoline-3-carboxylic acid;

6-[2-(2-phenyl-4-oxazolyl)ethoxy]-1,2,3,4-tetrahydro-N-benzyloxycarbonyl-isoquinoline-3-carboxylic acid, lithium salt 7-[2-(5-methyl-2-[2-furyl]-4-oxazolyl)ethoxy]-1,2,3,4-tetrahydo-N-phenylmethylsulfonyl-isoquinoline-3-carboxylic acid;

7-[2-(2-phenyl-4-oxazolyl)ethoxy]-1,2,3,4-tetrahydo-N-ethoxycarbonyl-isoquinoline-3-carboxamide;

7-[2-(2-phenyl-4-oxazolyl)ethoxy]-1,2,3,4-tetrahydro-N-(4-chlorophenyl)carbonyl-isoquinoline-3-carboxylic acid;

7-[2-(5-methyl-2-(1-naphthyl)-4-thiazolyl)ethoxy]-1,2,3,4-tetrahydro-N-propionoyl-isoquinoline-3-hydroxamic acid;

7-[2-(2-phenyl-4-oxazolyl)ethoxy]-1,2,3,4-tetrahydro-N-benzyloxycarbonyl-isoquinoline-3-carboxylic acid, free acid;

7-[2-(2-phenyl-4-oxazolyl)ethoxy]-1,2,3,4-tetrahydro-N-benzyloxycarbonyl-isoquinoline-3-carboxylic acid, sodium salt;

3-RS-7-[2-(2-phenyl-4-oxazolyl)ethoxy]-1,2,3,4-tetrahydro-N-benzyloxycarbonyl-isoquinoline-3-carboxylic acid, free acid;

3-RS-7-[2-(2-phenyl-4-oxazolyl)ethoxy]-1,2,3,4-tetrahydro-N-benzyloxycarbonyl-isoquinoline-3-carboxylic acid, sodium salt;

3-R-7-[2-(2-phenyl-4-oxazolyl)ethoxy]-1,2,3,4-tetrahydro-N-benzyloxycarbonyl-isoquinoline-3-carboxylic acid, free acid;

3-R-7-[2-(2-phenyl-4-oxazolyl)ethoxy]-1,2,3,4-tetrahydro-N-benzyloxycarbonyl-isoquinoline-3-carboxylic acid, sodium salt;

3-S-7-[2-(2-phenyl-4-oxazolyl)ethoxy]-1,2,3,4-tetrahydro-N-benzyloxycarbonyl-isoquinoline-3-carboxylic acid, free acid;

3-S-7-[2-(2-phenyl-4-oxazolyl)ethoxy]-1,2,3,4-tetrahydro-N-benzyloxycarbonyl-isoquinoline-3-carboxylic acid, sodium salt;

7-[2-(2-phenyl-4-oxazolyl)ethoxy]-1,2,3,4-tetrahydro-N-benzyloxycarbonyl-isoquinoline-3-carboxylic acid, potassium salt;

7-[2-(2-phenyl-4-oxazolyl)ethoxy]-1,2,3,4-tetrahydro-N-phenylcarbonyl-isoquinoline-3-carboxylic acid, free acid;

7-[2-(2-phenyl-4-oxazolyl)ethoxy]-1,2,3,4-tetrahydro-N-benzylcarbonyl-isoquinoline-3-carboxylic acid, free acid;

7-[2-(2-phenyl-4-oxazolyl)ethoxy]-1,2,3,4-tetrahydro-N-4-methylbenzylcarbonyl-isoquinoline-3-carboxylic acid, free acid;

7-[2-(2-phenyl-4-oxazolyl)ethoxy]-1,2,3,4-tetrahydro-N-para-chlorophenylcarbonyl-isoquinoline-3-carboxylic acid, free acid;

7-[2-(2-phenyl-4-oxazolyl)ethoxy]-1,2,3,4-tetrahydro-N-benzylsulfonyl-isoquinoline-3-carboxylic acid, free acid;

7-[2-(2-phenyl-4-oxazolyl)ethoxy]-1,2,3,4-tetrahydro-N-para-bromophenyloxycarbonyl-isoquinoline-3-carboxylic acid, free acid;

7-[2-(2-phenyl-4-oxazolyl)ethoxy]-1,2,3,4-tetrahydro-N-para-trifluoromethylphenyloxycarbonyl-isoquinoline-3-carboxylic acid, free acid;

7-[2-(2-phenyl-4-oxazolyl)ethoxy]-1,2,3,4-tetrahydro-N-para-trifluoromethylphenyloxycarbonyl-isoquinoline-3-carboxylic acid, free acid;

7-[2-(2-phenyl-4-oxazolyl)ethoxy]-1,2,3,4-tetrahydro-N-para-methoxyphenyloxycarbonyl-isoquinoline-3-carboxylicacid, free acid;

7-[2-(2-phenyl-4-oxazolyl)ethoxy]-1,2,3,4-tetrahydro-N-para-n-butylphenyloxycarbonyl-isoquinoline-3-carboxylic acid, free acid;

7-[2-(2-phenyl-4-oxazolyl)ethoxy]-1,2,3,4-tetrahydro-N-benzylaminocarbonyl-isoquinoline-3-carboxylic acid, free acid;

7-[2-(2-phenyl-4-oxazolyl)ethoxy]-1,2,3,4-tetrahydro-N-ethyloxycarbonyl-isoquinoline-3-carboxylic acid, free acid;

6-[2-(2-phenyl-4-oxazolyl)ethoxy]-1,2,3,4-tetrahydroisoquinoline-3-carbonitrile, hydrochloric acid salt;

7-[2-(2-phenyl-4-oxazolyl)ethylthio]-1,2,3,4-N-benzyloxycarbonyl-isoquinoline-3-carboxylic acid, sodium salt;

6-[2-(2-phenyl-4-thiazolyl)-n-hexylsulfinyl]-1,2,3,4-N-benzyloxycarbonyl-isoquinoline-3-carboxylic acid, sodium salt;

7-[2-(6-phenyl-2-pyridyl)-n-dodecylsulfonyl]-1,2,3,4-N-benzyloxycarbonyl-isoquinoline-3-carboxylic acid, potassium salt;

7-[2-(2-phenyl-4-oxazolyl)ethylsulfonamido]-1,2,3,4-N-benzyloxycarbonyl-isoquinoline-3-carboxylic acid, sodium salt;

7-[2-(2-phenyl-4-oxazolyl)octylcarboxamido]-1,2,3,4-N-benzyloxycarbonyl-isoquinoline-3-carboxylic acid, free acid; and 7-[2-(2-phenyl-4-oxazolyl)butylaminosulfonyl]-1,2,3,4-N-benzyloxycarbonyl-isoquinoline-3-carboxylic acid, free acid.

A series of Schemes is presented below to familiarize the reader with chemical reactions and intermediates in the synthesis of compounds of Formula I. All substituents previously defined have the same meanings in the Schemes below. The substituent "R" in the Schemes below represents a carboxyl-protecting group. The substituent "X" in the Schemes below represents leaving group, such as a halogen leaving group.

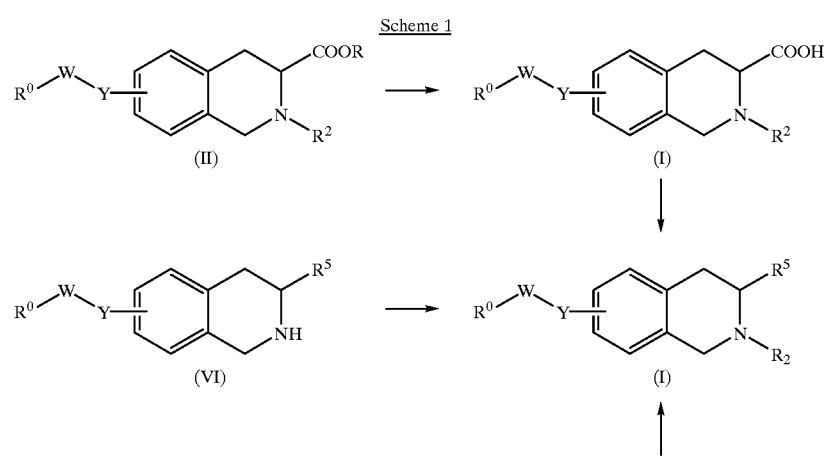

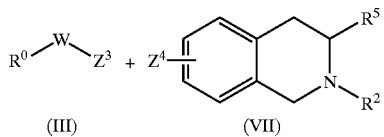

As described below in Schemes 2–4, compounds of Formula I wherein $R^5$ is —COOH, may be formed from compounds of Formula II by deprotecting the carboxyl group at position 3 of the 1,2,3,4-tetrahydroisoquinoline moiety, following methods described in Greene and Wuts, Chapter 5, and then, optionally, converting the —COOH group to another of the substituents of $R^5$. Compounds of Formula I wherein $R^2$ is other than hydrogen may be formed from compounds of Formula VI by adding an $R^2$ substituent at the nitrogen of the 1,2,3,4-tetrahydroisoquinoline moiety as described in Greene and Wuts, Chapter 7, or in Schemes 13 and 14 herein. Compounds of Formula I may also be formed by reacting a compound of Formula III with a compound of Formula VII, as elaborated in Schemes 5–9 herein.

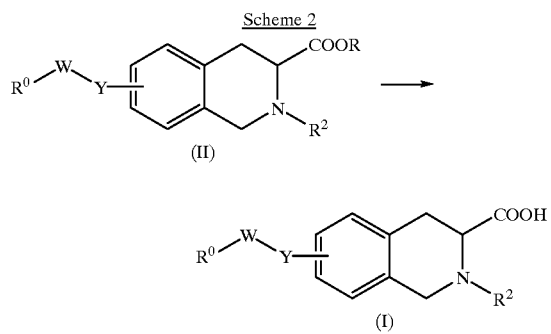

Compounds of Formula I wherein $R^5$ is —COOH may be derived from compounds of Formula II by deprotecting the 3-carboxylic acid group using methods described in Greene and Wuts, Chapter 5.

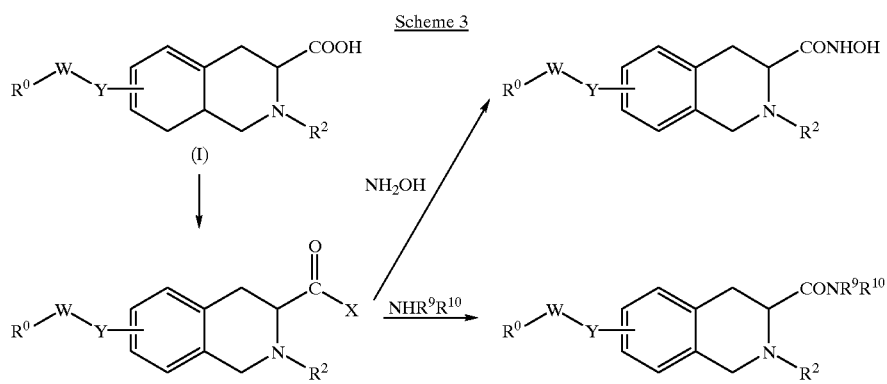

Optionally, a compound of Formula I wherein $R^5$ is —CONH$_2$, —CN, —CONHOH, or

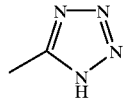

may be formed from compounds of Formula I wherein $R^5$ is —COOH. A first step is to form the acyl halide of (I) by reacting (I) wherein $R^5$ is —COOH with thionyl chloride, phosphorus pentachloride, or phosphorus tribromide. Reaction of the acyl halide of (I) with hydroxylamine yields (I) wherein $R^5$ is —CONHOH (the hydroxamate) (March, *Advanced Organic Chemistry*, McGraw-Hill, N.Y., 1968, page 335). Reaction of the acyl halide of (I) with ammonia, a primary amine, or secondary amine yields (I) wherein $R^5$ is —CONR$^9$R$^{10}$. (Sonntag, *Chem. Rev.* 52:258–294, 1953).

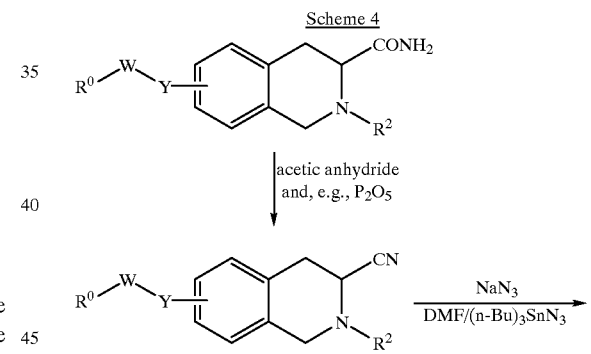

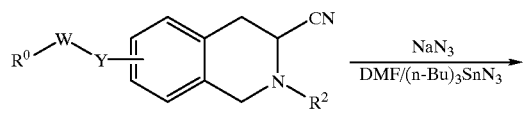

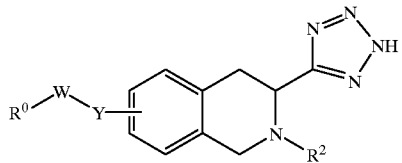

Treatment of a compound of Formula I wherein $R^5$ is —$CONH_2$ with an efficient dehydrating agent, such as $P_2O_5$, $POCl_3$, or $SOCl_3$, and acetic anhydride will convert it to a compound of Formula (I) wherein $R^5$ is —CN (Ugi, et al., *Angew. Chem. Intern. Ed. Engl.* 4:472–484, 1965; also, March, pages 777–778). A compound of Formula I wherein $R^5$ is

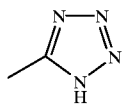

is made from a compound of Formula I wherein $R^5$ is —CN by reacting it with sodium azide in a solvent such as dimethylformamide at about 140 degrees Centigrade together with a tin reagent, such as tri-n-butyl tin azide (*Encyclopedia of Reagents for Organic Synthesis*, ed. by L. A. Paquette, J. H. Wiley & Sons, New York, 1995, vol. 7, pp. 5035–5037).

Scheme 5

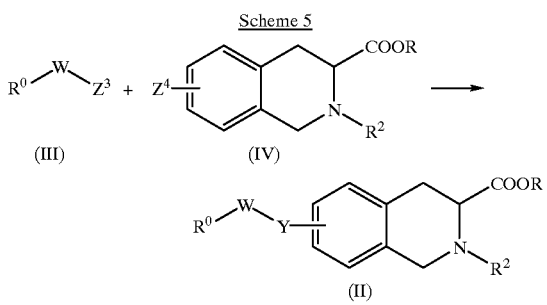

Compounds of Formula II may be made by addition of a compound of Formula III to a compound of Formula IV.

Substituent $Z^3$ of (III) and substituent $Z^4$ of (IV) are such that reaction of (III) and (IV) results in the formation of Y. Depending on the type of Y group sought, $Z^3$ may be —OH, —$SO_2Cl$, —X (halogen), —$NHR^9$, or —COCl and $Z^4$ may be —OH, —SH, —$NH_2$, or —$SO_2Cl$ for example. Scheme 5 shows the general reaction. Schemes 6–9 show the formation of specific Y groups. The table below shows the substituents $Z^3$ and $Z^4$ that might be selected for each group, Y. The particular selections of $Z^3$ and $Z^4$ are not meant to limit the groups that the skilled chemist might use to form Y of the compounds of Formula I.

| Y | $Z^3$ | $Z^4$ |
|---|---|---|
| —O— | —OH | HO— |
| —S— | —X | HS— |
| —SO— | —X | HS— |
| —$SO_2$— | —X | HS— |
| —NH— | —X | $_2$HN— |
| —$CONR^9$— | —COX | $HR^9N$— |
| —$SO_2NR^9$— | —$SO_2Cl$ | $_2$HN— |
| —$NR^9SO_2$— | —$NH_2$ | $ClO_2S$— |

Scheme 6

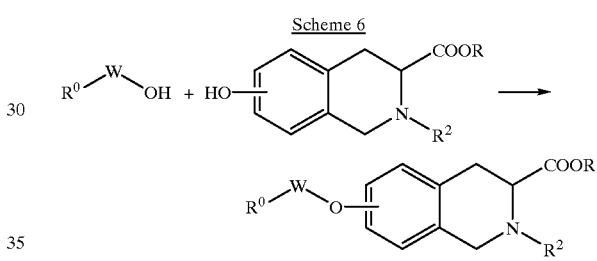

Where $Z^3$ is —OH, and $Z^4$ is —OH, compounds of Formula II wherein Y is —O— are synthesized by a standard method, such as the Mitsunobu reaction (*Synthesis*, p. 1, 1981; Hughes, D. L., *Organic Reactions* 42:336, 1992; Bose, A. K., et al., *J. Can. Chem.* 62:2498, 1984), as further exemplified in Example 1.

Scheme 7

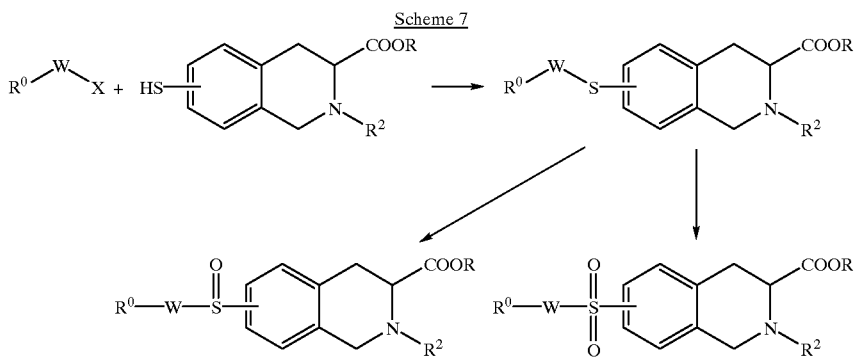

To obtain a thioether, wherein Y of (II) is —S—, $Z^3$ of (III) is —X (a halogen) and $Z^4$ of (IV) is —SH (March, page 1171). The compound of Formula II wherein Y is —SO— may be formed from the thioether by oxidation using one equivalent of hydrogen peroxide (March, page 887). The compound of Formula II wherein Y is —SO$_2$— may be formed from the thioether by further oxidation using two equivalents of hydrogen peroxide, or using potassium permanganate, or other oxidizing agents (March, page 887).

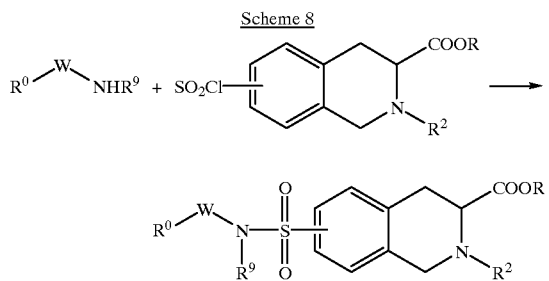

A compound of Formula (II) wherein Y is —NR$^9$SO$_2$— is formed by reaction of compound III wherein Z$^3$ is —NHR$^9$, and compound IV wherein Z$^4$ is —SO$_2$Cl (March, page 374).

Where Z$^3$ is —COX and Z$^4$ is —NH$_2$, compound (II) wherein Y is —CONH—, is formed by amidation of an acid chloride (March, page 335). Reaction of (III) wherein Z$^3$ is —X with (IV) wherein Z$^4$ is —NH$_2$, under conditions favorable for alkylation of the amine as described by March, page 331, results in the synthesis of (II) wherein Y is —NH—. A compound of Formula II wherein Y is —SO$_2$NH— is formed by reaction between a compound of Formula III wherein Z$^3$ is —SO$_2$Cl and a compound of Formula IV wherein Z$^4$ is —NHR$^9$ (March, page 374). A compound of Formula II wherein Y is —SO$_2$NR$^9$— or —CONR$^9$— may be subsequently formed using an alkyl halide (R$^9$—X) (March, page 340).

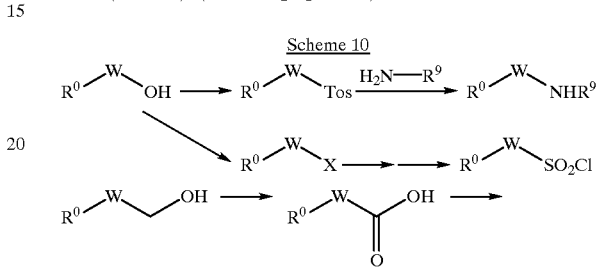

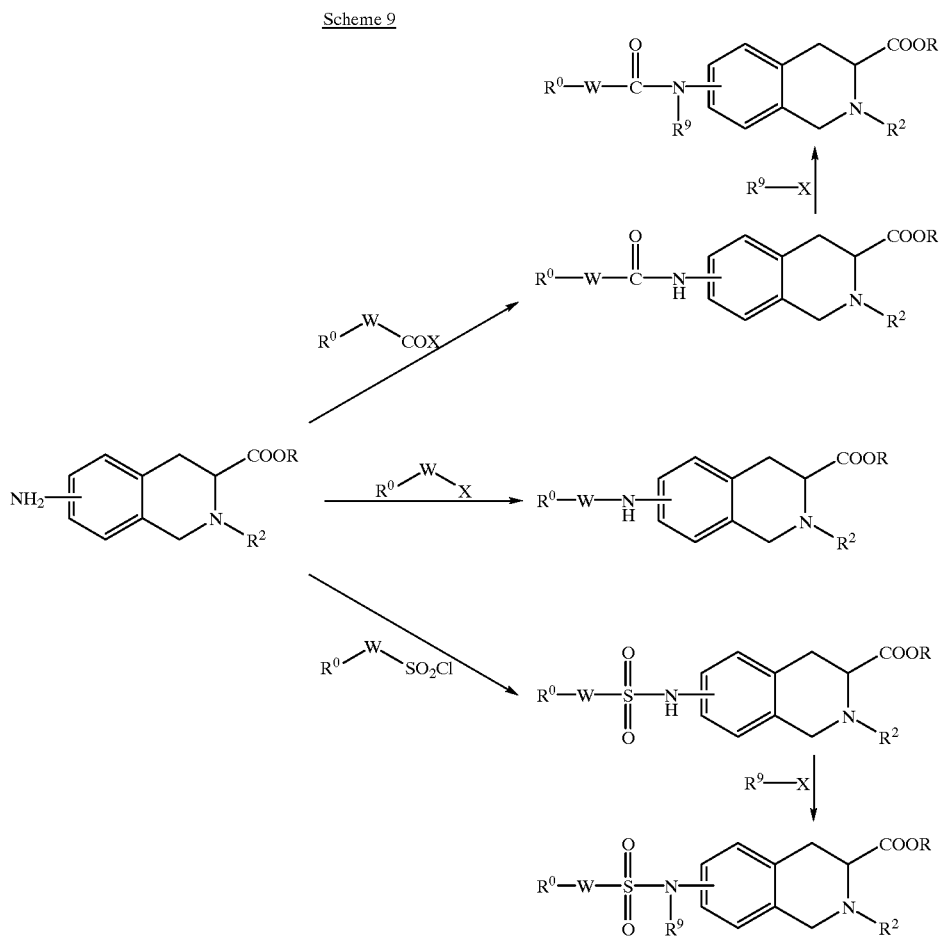

-continued

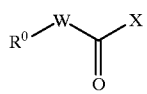

Compounds of Formula III are synthesized using known reactions (A. R. Katritsky, *Handbook of Heterocyclic Chemistry*, Pergamon Press, 1985). Compounds of Formula III wherein $Z^3$ is —$NHR^9$, —$SO_2Cl$, or —X may be made from a compound of Formula III wherein $Z^3$ is —OH (the alcohol). Where $Z^3$ is —$NHR^9$, the alcohol is converted to an amine, for example, by formation of a tosylate or mesylate followed by nucleophilic displacement with a substituted or unsubstituted amine (I. T. Harrison and S. Harrison, *Compendium of Organic Synthetic Methods*, Wiley-Interscience, New York, 1971, pp. 232, and 250–255). Where $Z^3$ is —$SO_2Cl$, the alcohol may be converted to a halide (March, p. 343), which on subsequent treatment with sodium bisulfite is converted to a sulfonic acid sodium salt (S. R. Sandler and W. Karo, *Organic Functional Group Preparations*, Academic Press, New York, 1968, p. 512). Treatment of the sulfonic acid sodium salt with chlorosulfonic acid, for example, then produces the sulfonyl chloride (Sandler and Karo, p, 517). Where $Z^3$ is —X, the alcohol is treated with a halogen acid, or an inorganic acid halide (March, page 343). To make a compound of Formula III wherein $Z^3$ is —COX, a compound of formula

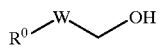

may be oxidized to an acid (Harrison and Harrison, pp. 26–30), from which the halide may be formed (Harrison and Harrison, pp. 18–22).

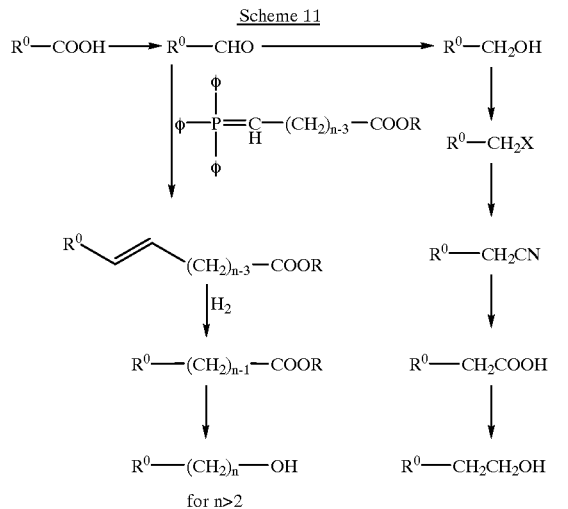

Scheme 11 shows syntheses of various alcohols used as starting material in Scheme 10. Partial reduction of the acid, $R^0$—COOH, to the aldehyde (Harrison and Harrison, pp. 132–137) followed by Wittig condensation (March, pp. 845—854), olefin reduction (Harrison and Harrison, pp. 198–202) and further reduction to the alcohol (Harrison and Harrison, pp. 76–78), with or without saponification, will produce $R^0$—$(CH_2)_n$—OH, for n greater than 2. Full reduction of the acid $R^0$—COOH, will produce $R^0$—$CH_2$—OH. The alcohol $R^0$—$CH_2$—OH may be homologated to $R^0$—$(CH_2)_2$—OH by standard methods, such as, conversion to halide (March, p. 343), displacement with cyanide (Harrison and Harrison, pp. 468–470), hydrolysis of the resulting nitrile to a carboxylic acid (Harrison and Harrison, pp. 62–64), and reduction of the acid to the alcohol (Harrison and Harrison, pp. 76–78).

Where $R^0$ is

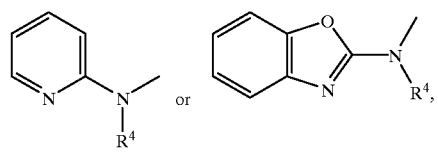

the intermeidate of the form $R^0$—$(CH_2)_n$—OH may be synthesized following Cantello, et al., *J. Med. Chem.*, 37:3977–3985, 1994.

Where $R^0$ is

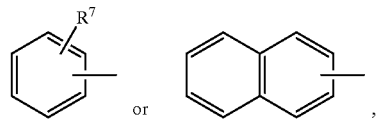

the reactions of Scheme 11 are followed, starting with readily-available carboxylic acid, aldehyde, or alcohol derivatives of $R^0$.

Scheme 12

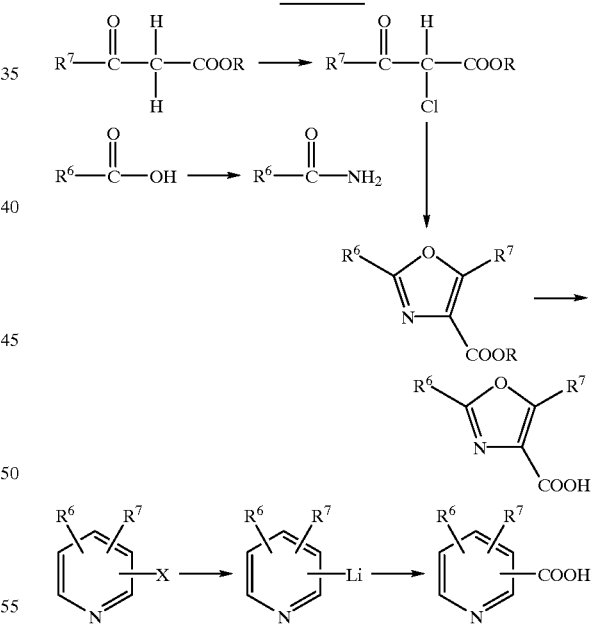

Scheme 12 demonstrates a method to form groups of the form $R^0$—COOH which are used in Scheme 11. Where $R^0$ is thiazole the method of L. A. Paquette, *Principles of Modern Heterocyclic Chemistry*, W. A. Benjamin, 1968, page 191, may be followed. A substituted thiazole may be obtained using the same scheme, but substituting the corresponding thioamide, following Paquette, page 193. The pyridyl intermediate of form $R^0$—COOH may be prepared by the method of E. H. Rood, ed., Chemistry of Carbon Compounds, Vol. IV$^A$, Elsevier Publ. Co., 1957, page 557.

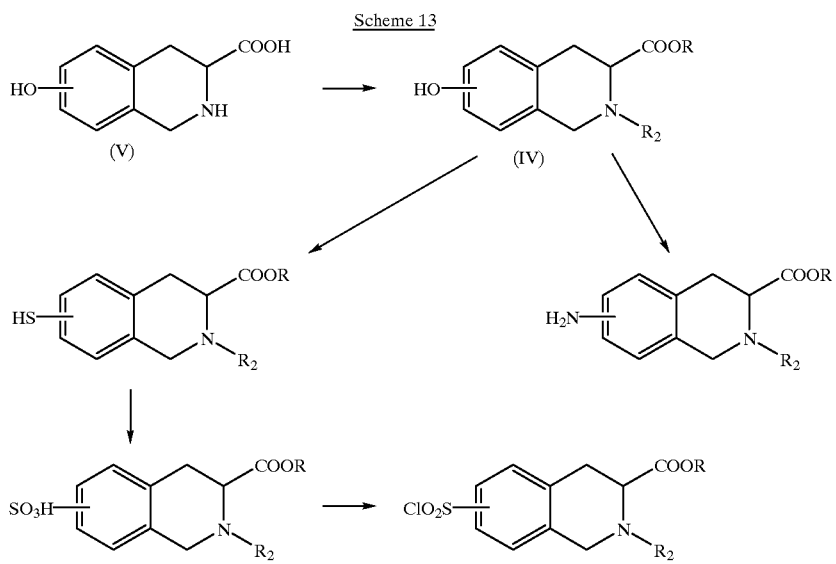

Scheme 13

A convenient starting material for synthesis of compounds of Formula IV, which are compounds wherein substituent "Y" is attached at the 6 position or at the 7 position of the 1,2,3,4-tetrahydroisoquinoline ring, is the compound of Formula V, specifically, either 7-hydroxy-1,2,3,4-tetrahydroisoquinoline-3-carboxylic acid or 6-hydroxy-1,2,3,4-tetrahydroisoquinoline-3-carboxylic acid. Both named compounds are readily available as racemates or either pure enantiomer, or may be synthesized (Synthesis #5, 458–460, 1992, and also Scheme 15, herein).

To form the compounds of Formula IV, the carboxy and amino groups of Formula V are protected or derivatized. The 3-carboxylic acid group is protected by a carboxy-protecting group, R, following Greene and Wuts, Chapter 5. The nitrogen atom is either protected or is derivatized by any of the substituents, $R^2$, using methods in Greene and Wuts, Chapter 7.

After both the carboxy and amino groups are protected or derivatized, the aromatic hydroxy group may be optionally transformed by known reactions to form other compounds of Formula IV, wherein $Z^4$ is —SH, —$NH_3$, or —$SOCl_2$. For example, the amine derivative is formed using 4-chloro-2-phenylquinazoline (Fieser and Fieser, 4, 86). The compound of Formula IV wherein $Z^4$ is —SH may be formed by treating a compound of Formula IV wherein $Z^4$ is —OH with dimethylthiocarbamyl halide in the presence of hydroxide ion at elevated temperature using Newman's method (Fieser and Fieser 4, 202). A compound of Formula IV wherein $Z^4$ is —$SO_3$ is formed from a compound of Formula IV wherein $Z^4$ is —SH by oxidation.

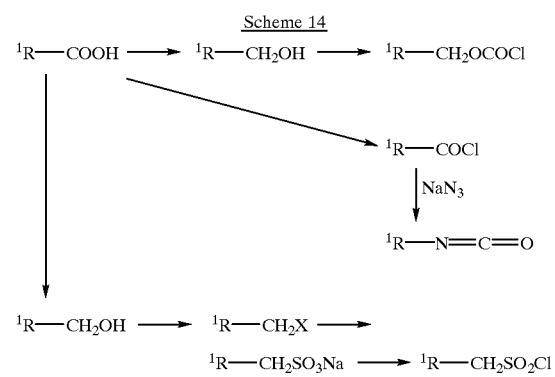

Scheme 14

Reagents for attaching the substituent $R^2$ to the nitrogen atom of the 1,2,3,4-tetrahydroisoquinoline moiety may be prepared as shown in Scheme 14, or may be found in Greene and Wuts, Chapter 7. For example, where it is desired that $R^2$ be a $C_{1-4}$ alkyloxycarbonyl or an aryl $C_{1-4}$ alkyloxycarbonyl group, the synthesis of Scheme 14 could start with the corresponding $C_{0-11}$ alkyl acid or aryl $C_{0-3}$ alkyl acid. The acid could be reduced to the alcohol, and the alcohol reacted with phosgene and base, for example, to yield the corresponding oxycarbonyl chloride. Alternatively, the corresponding alcohol could serve as the starting point if it were available.

An acyl halide or an aryl acyl halide may be used to form the compound of Formula I wherein $R_2$ is $C_{1-4}$ acyl or aryl $C_{1-4}$ acyl. The acyl halide is formed from the acid by standard methods, such as reaction of the acid with thionyl chloride, phosphorus pentachloride, or phosphorus tribromide.

An isocyanate derivative may be used to form the compound of Formula I wherein $R^2$ is $C_{1-4}$ alkylaminocarbonyl, arylaminocarbonyl, or aryl $C_{1-4}$ alkylaminocarbonyl. The isocyanate may be formed from the acid halide by reaction with sodium azide (Fieser and Fieser, 1, 1041).

A sulfonyl chloride reagent may be used to create the compound of Formula I wherein $R^2$ is aryl $C_{1-4}$ alkylsulfonyl. The sulfonyl chloride reagent may be formed from an acid by reducing the acid to an alcohol, and then following the sequence described in Scheme 14.

In Scheme 14, $R^1$ is a group such that reaction between a compound at the right side of Scheme 13 and the free nitrogen atom of the 1,2,3,4-tetrahydroisoquinoline moiety, or a derivative thereof, leaves a group defined as $R^2$ attached to said nitrogen atom. The relation between the groups $R^1$, $R^2$, and the compound used to derivatize the nitrogen atom of the 1,2,3,4-tetrahydroisoquinoline moiety are shown for some representative groups in the table below.

| $R^2$ | $R^1$ | Compound to Derivative Nitrogen Atom |
|---|---|---|
| benzyloxycarbonyl | phenyl | $R^1$—$CH_2$—O—COCl |
| phenylcarbonyl | phenyl | $R^1$—COCl |
| benzylcarbonyl | benzyl | $R^1$—COCl |
| ethyloxycarbonyl | ethyl | $R^1$—O—COCl |
| n-butylaminocarbonyl | n-butyl | $R^1$—N=C=O |
| phenylmethylsulfonyl | phenyl | $R^1$—$CH_2$—$SO_2Cl$ |

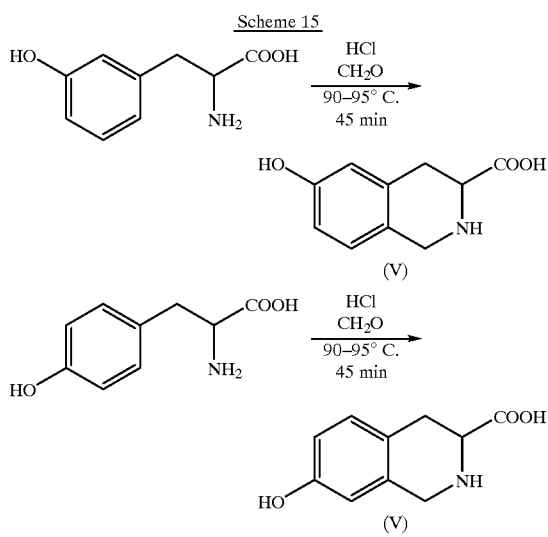

The compound of formula (V), used as starting material in Scheme 13, wherein the hydroxy group is attached at the 6-position of 1,2,3,4-tetrahydroisoquinoline, may be made from 3-hydroxyphenylalanine following the directions in Example 1 of U.S. Pat. No. 4,902,695, herein incorporated expressly by reference. Likewise, the compound of formula (V) wherein the hydroxy group is attached at the 7-position of the 1,2,3,4-tetrahydroisoquinoline may be made from tyrosine (4-hydroxyphenylalanine) following the directions in the same reference.

The compounds of the present invention can be administered in oral forms, such as, without limitation, tablets, capsules, pills, powders, granules, elixirs, tinctures, suspensions, syrups, and emulsions. They may also be administered in parenteral forms, such as, without limitation, intravenous (bolus or infusion), intraperitoneal, subcutaneous, intramuscular, and the like forms, well-known to those of ordinary skill in the pharmaceutical arts. The compounds of the present invention can be administered in intranasal form via topical use of suitable intranasal vehicles, or via transdermal routes, using transdermal delivery systems well-known to those of ordinary skill in that art.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

The compounds of the present invention are preferably formulated prior to administration together with one or more pharmaceutically-acceptable excipients. Excipients are inert substances such as, without limitation carriers, diluents, flavoring agents, sweeteners, lubricants, solubilizers, suspending agents, binders, tablet disintegrating agents and encapsulating material.

Therefore, yet another embodiment of the present invention is a pharmaceutical formulation comprising a compound of the invention and one or more pharmaceutically-acceptable excipients that are compatible with the other ingredients of the formulation and not deleterious to the recipient thereof. Pharmaceutical formulations of the invention are prepared by combining (e.g., mixing) a therapeutically effective amount of the compounds of the invention together with one or more pharmaceutically-acceptable excipients therefor. In making the compositions of the present invention, the active ingredient may be admixed with a diluent, or enclosed within a carrier, which may be in the form of a capsule, sachet, paper, or other container. The carrier may serve as a diluent, which it may be solid, semi-solid, or liquid material which acts as a vehicle, or can be in the form of tablets, pills, powders, lozenges, elixirs, suspensions, emulsions, solutions, syrups, aerosols (as a solid or in a liquid medium), ointments, containing, for example, up to 10% by weight of the active compound, soft and hard gelatin capsules, suppositories, sterile injectable solutions and sterile packaged powders.

For oral administration in the form of a tablet or capsule, the active ingredient may be combined with an oral, non-toxic, pharmaceutically-acceptable carrier, such as, without limitation, lactose, starch, sucrose, glucose, methyl cellulose, calcium carbonate, calcium phosphate, calcium sulfate, sodium carbonate, mannitol, sorbitol, and the like; together with, optionally, disintegrating agents, such as, without limitation, maize, starch, methyl cellulose, agar, bentonite, xanthan gum, alginic acid, and the like; and, optionally, binding agents, for example, without limitation, gelatin, acacia, natural sugars, betalactose, corn sweeteners, natural and synthetic gums, acacia, tragacanth, sodium alginate, carboxymethylcellulose, polyethylene glycol, waxes, and the like; and, optionally, lubricating agents, for example, without limitation, magnesium stearate, sodium stearate, stearic acid, sodium oleate, sodium benzoate, sodium acetate, sodium chloride, talc, and the like.

In powders, the carrier is a finely divided solid which is in admixture with the finely divided active ingredient. In tablets, the active ingredient is mixed with a carrier having the necessary binding properties in suitable proportions and compacted in the shape and size desired. The powders and tablets preferably contain from about 1 to about 99 weight percent of the active ingredient which is the novel composition of the instant invention. Suitable solid carriers are magnesium carbonate, magnesium stearate, talc, sugar, lactose, pectin, dextrin, starch, gelatin, tragacanth, methylcellulose, sodium carboxymethyl cellulose, low melting waxes, and cocoa butter.

Sterile liquid formulations include suspensions, emulsions, syrups, and elixirs. The active ingredient can be dissolved or suspended in a pharmaceutically acceptable carrier, such as sterile water, sterile organic solvent, or a mixture of both sterile water and sterile organic solvent.

The active ingredient can also be dissolved in a suitable organic solvent, for example, aqueous propylene glycol. Other compositions can be made by dispersing the finely divided active ingredient in aqueous starch or sodium carboxymethyl cellulose solution or in a suitable oil.

Preferably, the pharmaceutical formulation is in unit dosage form. A "unit dosage form" is a physically discrete unit containing a unit dose, suitable for administration in human subjects or other mammals. A unit dosage form can be a capsule or tablet, or a number of capsules or tablets. A "unit dose" is a predetermined quantity of the active compound of the present invention, calculated to produce the desired therapeutic effect, in association with one or more pharmaceutically-acceptable excipients. The quantity of active ingredient in a unit dose may be varied or adjusted from about 0.1 to about 1000 milligrams or more according to the particular treatment involved. It may be appreciated that it may be necessary to make routine variations to the dosage depending on the age and condition of the recipient. The dosage will also depend on the route of administration.

The oral route is most preferred. Typical oral dosages of the present invention, when used for the indicated effects, will range from about 0.01 mg per kg body weight per day (mg/kg/day) to about 50 mg/kg/day, preferably from 0.1 mg/kg/day to 30 mg/kg/day, and most preferably from about 0.5 mg/kg/day to about 10 mg/kg/day. The compounds of the present invention may be administered in a single daily dose, or the total daily dose may be administered in divided doses, two, three, or more times per day. Where delivery is via transdermal forms, of course, administration is continuous.

Administration to a human is most preferred. The human to whom the compounds and formulations of the present invention are administered has a disease or condition in which control blood glucose levels are not adequately controlled without medical intervention, but wherein there is endogenous insulin present in the human's blood. Noninsulin dependent diabetes mellitus (NIDDM) is a chronic disease or condition characterized by the presence of insulin in the blood, even at levels above normal, but resistance or lack of sensitivity to insulin action at the tissues. The compounds and formulations of the present invention are also useful to treat acute or transient disorders in insulin sensitivity, such as sometimes occur following surgery, trauma, myocardial infarction, and the like. The compounds and formulations of the present invention are also useful for lowering serum triglyceride levels. Elevated triglyceride level, whether caused by genetic predisposition or by a high fat diet, is a risk factor for the development of heart disease, stroke, and circulatory system disorders and diseases. The physician of ordinary skill will know how to identify humans who will benefit from administration of the compounds and formulations of the present invention.

The following formulation examples are illustrative only and are not intended to limit the scope of the invention in any way.

FORMULATION 1

Hard gelatin capsules are prepared by mixing the following ingredients and filling the mixture, in 460 mg quantities, into hard gelatin capsules.

| Ingredient | Quantity (mg/capsule) |
| --- | --- |
| 7-[2-(2-phenyl-4-oxazolyl)ethoxy]-1,2,3,4-tetrahydro-N-benzyloxycarbonyl-isoquinoline-3-carboxylic acid, free acid | 250 |
| Starch, dried | 200 |
| Magnesium stearate | 10 |
| Total | 460 |

FORMULATION 2

A tablet containing 250 mg of the compound of the present invention is prepared by blending the components listed below and then compressing 665 mg of the blend into a tablet.

| Ingredient | Quantity (mg/tablet) |
| --- | --- |
| 7-[2-(2-phenyl-4-oxazolyl)ethoxy]-1,2,3,4-tetrahydro-N-benzyloxycarbonyl-isoquinoline-3-carboxylic acid, sodium salt | 250 |
| Cellulose, microcrystalline | 400 |
| Silicon Dioxide, fumed | 10 |
| Stearic Acid | 5 |
| Total | 665 |

FORMULATION 3

A tablet containing 60 mg of the compound of the present invention is prepared as follows:

| Ingredient | Quantity (mg/tablet) |
| --- | --- |
| 7-[2-(2-phenyl-4-oxazolyl)ethoxy]-1,2,3,4-tetrahydro-N-benzyloxycarbonyl-isoquinoline-3-carboyxlic acid, potassium salt | 60 |
| Starch | 45 |
| Cellulose, microcrystalline | 35 |
| Polyvinylpyrrolidone, 10%, aqueous | 4 |
| Sodium carboxymethyl starch | 4.5 |
| Magnesium stearate | 0.5 |
| Talc | 1 |
| Total | 150 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxylmethyl starch, magnesium stearate, and talc, previously passed though a No. 60 mesh U.S. sieve, are then added to the granules which, after mixing, are compressed on a tablet machine to yield tablets each weighing 150 mg.

FORMULATION 4

Capsules containing 80 mg of the active compound of the present invention are made as follows:

| Ingredient | Quantity (mg/capsule) |
| --- | --- |
| 6-[2-(2-phenyl-4-thiazolyl)ethylsulfinyl]-1,2,3,4-tetrahydroisoquinoline-3-carbonitrile, hydrochloride | 80 |
| Starch | 59 |
| Cellulose, microcrystalline | 59 |
| Magnesium stearate | 2 |
| Total | 200 |

The active ingredient, starch, cellulose, and magnesium stearate are blended, the blend is passed through a No. 45 mesh U.S. sieve, and then hard gelatin capsules are filled with 200 mg of the blend.

FORMULATION 5

Suppositories each containing 225 mg of active compound of the present invention are made as follows:

| Ingredient | Quantity (mg/suppository) |
| --- | --- |
| 7-[2-(5-butyl-2-(2-naphthyl)-4-oxazolyl)ethoxy]-1,2,3,4-tetrahydro-N-para-chlorobenzylcarbonyl-isoquinoline-3-carboxylic acid | 225 |
| Saturated fatty acid glycerides | 2,000 |
| Total | 2,225 |

The active compound is passed through a No. 60 mesh U.S. sieve and suspended in the saturated fatty acid glycerides, previously melted using the minimum heat necessary. The mixture is then poured into a suppository mold of nominal 2 g capacity and allowed to cool.

FORMULATION 6

Suspensions each containing 50 mg of active compound of the present invention per 5 mL dose are made as follows:

| Ingredient | Quantity per dose |
| --- | --- |
| 7-[2-(5-methyl-2-(2-furyl)-4-oxazolyl)ethoxy]-1,2,3,4-tetrahydro-N-phenylmethylsulfonyl-isoquinoline-3-carboxylic acid | 50 mg |
| SOdium Carboxymethyl Cellulose | 50 mg |
| Syrup | 1.25 mL |
| Benzoic Acid Solution | 0.10 mL |
| Flavor | q.v. |
| Color | q.v. |
| Purified Water to total volume: | 5 mL |

The active ingredient, starch, cellulose, and magnesium stearate are blended, the blend is passed through a No. 45 mesh U.S. sieve, and then hard gelatin capsules are filled with 200 mg of the blend.

FORMULATION 7

An intravenous formulation may be prepared as follows:

| Ingredient | Quantity |
| --- | --- |
| 7-[2-(2-(2,5-dimethyl-4-pyridyl)-4-oxazolyl)ethoxy]-1,2,3,4-tetrahydro-N-phenylmethylsulfonyl-isoquinoline-3-tetrazole, sodium salt | 100 mg |
| Sterile, isotonic saline | 1000 mL |

The compound of the present invention is dissolved in the saline and administered intravenously at a rate of 1 mL per minute to a subject in need thereof.

FORMULATION 8

An aerosol solution is prepared by mixing the active ingredient with ethanol and then with the propellant 22, cooled to −30° C., and transferred to a filling device. The required amount is then fed to a stainless steel container and diluted with the remainder of the propellant. The valve units are finally fitted to the container.

| Ingredient | Weight % |
| --- | --- |
| 7-[4-(2-benzyl-4-oxazolyl)butylaminosulfonyl]-1,2,3,4-N-benzylcarbonyl-isoquinoline-3-carboxylic acid, free acid | 0.25 |
| Ethanol | 29.75 |
| Propellant 22 | 70.00 |
| Total | 100.00 |

EXAMPLES

Melting points were measured using a Thomas Hoover capillary instrument and are uncorrected. Ratios are on a weight basis, except fluid mixtures for chromatography, which are on a volume basis. Temperatures are in degrees Celsius. Chromatography was performed on silica under low or medium pressure "flash" conditions as described by C. W. Still, et al., *J. Org. Chem.* 43:2923 (1978). Thin Layer Chromatography (TLC) was performed on glass plates coated with silica gel, 240 microns, grade 2.

Proton NMR spectra were obtained using a QE 300 at 300.15 MHz and peak positions are reported as delta values relative to an internal TMS standard.

The following abbreviations for common solvents, reagents and substituent groups are used throughout:

h, hour(s)

rt, room temperature (ca. 25°)

mM, millimole(s)

mL, millimeters

MeOH, methanol

EtOH, ethanol

THF, tetrahydrofuran

NaH, sodium hydride

DEAD, diethyl azodicarboxylate

DIAD, di-isopropyl azodicarboxylate

1-HOBT-NH$_3$, 1-Hydroxybenzotriazole-Ammonia Complex

EtOAc, ethyl acetate
HOAc, acetic acid
$H_2O$, water
$H_2O_2$, hydrogen peroxide
$Na_2SO_4$, sodium sulfate (anhydrous)
$MgSO_4$, magnesium sulfate (anhydrous)
NaOH, sodium hydroxide
HCl hydrochloric acid
DCC, Dicyclohexyl carbodiimide
DMF, Dimethyl formamide
$CH_2Cl_2$, dichloromethane
$CHCl_3$, chloroform
Cbz, benzyloxycarbonyl
Bz, benzoyl
Ac, acetyl Preparation 1

2-(2-Phenyl-4-oxazolyl)ethanol.

To an ice-cooled suspension of 5.87 g (0.155 mol) of $LiAlH_4$ in 700 mL of $Et_2O$ was added a solution of 35.53 g (0.154 mol) of ethyl 2-phenyl-4-oxazoleacetate in 300 mL of $Et_2O$ over a 1.5 hour period. The temperature of the reaction during the addition was kept below 15° C. After stirring for 2 hours at 25° C. the reaction was decomposed by the addition of 15 mL of EtOAc and 33.5 mL of water. The mixture was filtered through anhydrous $Na_2SO_4$ and concentrated in vacuo to leave 28.1 g of oil. Distillation of the crude oil gave 2-(2-phenyl-4-oxazolyl)ethanol (23.52 g, 81%, b.p. 120–122° C./0.05–0.06 mm) as an oil which solidified on standing.

Anal. Cal. for $C_{11}H_{11}NO_2$: C, 69.83; H, 5.86; N, 7.40; Found: C, 69.78; H, 5.90; N, 7.49;

Example 1

7-[2-(2-Phenyl-4-oxazolyl)ethoxy]-L-1,2,3,4-tetrahydro-N-CBZ-isoquinoline-3-carboxylic acid.

Part A.

7-Hydroxy-1,2,3,4-tetrahydroisoquinoline-3-carboxylic acid.

The synthesis of 7-hydroxy-1,2,3,4-tetrahydroisoquinoline-3-carboxylic acid is accomplished by the method described in Synthesis (1992) #5, 458–460, or as in Example 1 of U.S. Pat. No. 4,902,695, starting with tyrosine.

Five (5) g (25 mM) of 7-hydroxy-1,2,3,4-tetrahydroisoquinoline-3-carboxylic acid (Peptides International, Inc.) was combined with 1.02 g (25.88 mM) of NaOH, 200 mL of $H_2O$:dioxane (1:1), and 20 mg of phenolphthalein. The mixture was cooled to −5° C. and alternating drop-wise additions of 9 mL (63.0 mM) of CBZ-Cl and ~25.3 mL (63.0 mM) of 2.5N NaOH were made to maintain pH 9–10. When the addition was complete, the reaction was stirred at −5° C. for 8 h and then was allowed to warm to ambient temperature overnight. The reaction mixture was neutralized to pH~7 with conc. HCl and concentrated under reduced pressure to a dark rose colored oil. This residue was diluted with 200 mL of MeOH:$H_2O$ (1:1) and treated with 3.1 g (77 mM) of solid NaOH. The resulting solution was stirred at ambient temperature for 48 h. After conc. HCl was added to pH~2, solvent was removed under reduced pressure (50° C.). The resulting white solid was taken up in EtOAc and washed with $H_2O$, then brine, and finally dried over $MgSO_4$. The dried organic layer was then filtered and concentrated to a clear oil which was purified by column chromatography. All non-polar impurities were eluted with 15:2 $CHCl_3$:MeOH containing 1% $NH_4OH$ and the product was eluted with acetone:MeOH (5:1). Pure fractions were collected, concentrated, diluted in 300 mL EtOAc and washed with 300 mL 2N HCl, 2×200 mL $H_2O$, dried over $MgSO_4$, filtered and concentrated to a wine colored oil. The oil was dried under vacuum to afford 5.9 g (69.7%) of dry white foam.

5.9 g (18 mM) of the product prepared above was dissolved in 125 mL of dry methanol and treated with 1 mL of AcCl. The mixture was stirred for 16 h at ambient temperature, concentrated to a clear oil, diluted with 300 mL EtOAc, washed with 2×300 mL $H_2O$, 200 mL brine and dried over $MgSO_4$. The extracts were filtered, concentrated to a clear oil, and eluted through a silica plug with 100% EtOAc. The eluent was stripped to dryness leaving 5.5 g (89%) of a waxy white solid, used directly in Part B.

Part B 4.5 g (13 mM) of the product prepared in Part A, 3.46 g (13 mM) of $PPh_3$, and 2.50 g (13.18 mM) of 2-(2-phenyl-4-oxazlyl)ethanol were dissolved in 200 mL of dry THF, treated drop-wise with 2.6 mL (13 mM) of DIAD and stirred for 16 h at ambient temperature. The mixture was then concentrated to an amber oil under reduced pressure. The product was recovered from the oil via column chromatography, using a gradient starting with 5:1 Hex:EtOAc and ending with 3.5:1 Hex:EtOAc. The recovered waxy solid was saponified by dissolving in 250 mL of 5:1 MeOH:$H_2O$, treating with 2.7 g of solid NaOH and stirring at ambient temperature for 16 h. The reaction mixture was acidified to pH~2 and concentrated under reduced pressure. The aqueous solution was extracted with EtOAc (3×200 mL) and the combined extracts were washed with $H_2O$, then brine, then dried over $MgSO_4$, filtered, stripped, and dried to a sticky solid. The gum was triturated with dry pentane (5×250 mL) for 24 hr to afford 2.3 g (35%) of a dry white powder.

m.p. 179–182°; Anal: Cal. for $C_{29}H_{26}N_2O_6$: C, 69.87; H, 5.26; N, 5.62. Found: C, 69.73; H, 5.48; N, 5.52; MS: m/z 499; by FDMS. IR: (KBr)1707 , 1620 $cm^{-1}$; $^1HNMR$ (DMSO-$d_6$): δ2.99 (m, 2H), 3.09 (m, 2H), 4.25 (m, 2H), 4.20–4.54 (m, 2H), 4.85–4.95 (m, 1H), 5.13–6.02 (m, 2H), 6.79 (m, 1H) 6.90 (m, 1H), 7.12 (m, 1H), 7.30–7.45 (m, 5H), 7.54 (m, 3H), 7.95 (m, 2H), 8.03 (s, 1H).

Example 2

7-[2-(2-Phenyl-4-oxazolyl)ethoxyl]-L-1,2,3,4-tetrahydro-N-CBZ-isoquinoline-3-carboxylic acid, sodium salt.

Six hundred mg (1.2 mMol) of the free acid prepared in Example 1 was added to a solution of 0.048g (1.2 mMol) of NaOH in 50 mL $H_2O$ and stirred for 0.5 h at ambient temperature. The mixture was concentrated in vacuo, purified using reverse-phase C18 Silica chromatography (eluting with a gradient of 5% MeCN/$H_2O$- - -70% MeCN/$H_2O$) and lyophilized to provide 0.60 g (90%) of white fluffy solid.

mp.90–94° C.; Anal: Cal. for $C_{29}H_{25}N_2O_6Na$: C, 66.92; H, 4.84; N, 5.38; Found: C, 67.02; H, 5.10; N, 5.61; MS (FAB+) 521.4; IR (KBr) 1683, 1595 $cm^{-1}$; NMR (DMSO-$d_6$) 2.80 (m, 1H), 2.98 (t, 2H), 3.22 (m, 1H), 4.21 (t, 3H), 4.45–4.64 (m, 3H), 5.05 (m, 2H), 6.70 (m, 2H), 6.97 (m, 1H), 7.25–7.43 (m, 5H), 7.63 (m, 3H), 7.96 (m, 2H), 8.05 (m, 1H).

Example 3

7-[2-(2-Phenyl-4-oxazolyl)ethoxy]-1,2,3,4-tetrahydro-N-ethyloxycarbonyl-isoquinoline-3-carboxylic acid.

The procedure of Example 1 is followed, substituting ethylchloroformate for CBZ-Cl in Part A of Example 1.

Example 4

7-[2-(5-Methyl-2-phenyl-4-oxazolyl)ethoxy]-1,2,3,4-tetrahydro-N-benzylsulfonyl-isoquinoline-3-carboxylic acid.

The procedure of Example 1 is followed, substituting toluenesulfonyl chloride for CBZ-Cl in Part A of Example 1.

Example 5
7-[2-(2-phenyl-4-oxazolyl)ethoxy]-1,2,3,4-tetrahydro-N-para-chlorobenzyloxycarbonyl-isoquinoline-3-carboxylic acid.

The procedure of Example 1 is followed, substituting para-chlorobenzyl chloroformate for CBZ-Cl in Part A of Example 1.

Example 6
7-[2-(5-Methyl-2-phenyl-4-oxazolyl)ethoxy]-1,2,3,4-tetrahydro-N-CBZ-isoquinoline-3-carboxylic acid.

The procedure of Example 1 is followed, substituting 2-(5-methyl-2-phenyl-4-oxazolyl)ethanol for 2-(2-phenyl-4-oxazolyl)ethanol in Part B of Example 1.

Example 7
7-[2-(2-Phenyl-4-oxazolyl)ethoxy]-1,2,3,4-tetrahydro-N-phenylcarbonyl-isoquinoline-3-carboxylic acid.

The procedure of Example 1 is followed, substituting benzoyl chloride for CBZ-Cl in Part A of Example 1.

Example 8
7-[2-(2-Phenyl-4-oxazolyl)ethoxy]-1,2,3,4-tetrahydro-N-phenylacetyl-isoquinoline-3-carboxylic acid.

The procedure of Example 1 is followed, using phenylacetyl chloride in place of CBZ-Cl in Part A of Example 1.

Example 9
7-[2-(2-Phenyl-4-oxazolyl)ethoxy]-1,2,3,4-tetrahydro-N-methylbenzoyl-isoquinoline-3-carboxylic acid.

The procedure of Example 1 is followed, using para-methylbenzoyl chloride in place of CBZ-Cl in Part A of Example 1.

Example 10
7-[2-(2-Phenyl-4-oxazolyl)ethoxy]-1,2,3,4-tetrahydro-N-CBZ-isoquinoline-3-carboxamide.

The product of Example 1 is added to dry DMF and cooled to 0° C. Solid DCC is added all at once. Finally, HOBT.NH$_3$ is added and the reaction mixture is allowed to stir at 0° C. for 1 h, and then at ambient temperature for 2 h. After concentration, the solution is diluted with H$_2$O, extracted 3× with EtOAc, washed brine, and finally dried over NaSO$_4$.

Example 11
7-[2-(2-Phenyl-4-oxazolyl)ethoxy]-1,2,3,4-tetrahydro-N-CBZ-isoquinoline-3-hydroxamic acid.

The product of Example 1 and a large molar excess of hydroxylamine hydrochloride are dissolved in MeOH and treated with an aqueous solution of potassium carbonate. The resulting mixture is stirred at ambient temperature for 3 h. The solvent is then removed under reduced pressure at ~35° C. The remaining solid is triturated 3× with H$_2$O, filtered, dried, dissolved in 20 mL of hot DMF and diluted with ~100 mL diethyl ether. The desired hydroxamate is recovered by chilling.

Example 12
7-[2-(2-Phenyl-4-oxazolyl)ethoxy]-1,2,3,4-tetrahydro-N-4-chlorobenzoyl-isoquinoline-3-carboxylic acid.

The procedure of Example 1 was followed, using 4-chlorobenzoyl chloride in place of CBZ-Cl in Part A of Example 1.

Example 13
7-[2-(2-Phenyl-4-oxazolyl)ethoxy]-1,2,3,4-tetrahydro-N-Phenylmethylsulfonyl-isoquinoline-3-carboxylic acid.

The procedure of Example 1 is followed, using phenylmethylsulfonic chloride in place of CBZ-Cl in Part A of Example 1.

Example 14
7-[2-(2-Phenyl-4-oxazolyl)ethoxy]-1,2,3,4-tetrahydro-N-(4-bromobenzyl)oxycarbonyl-isoquinoline-3-carboxylic acid.

Part A. (4-Bromobenzyl)-(4-nitrophenyl) carbonate.

(4-Bromobenzyl)-(4-nitrophenyl) carbonate was prepared by the methods of Letsinger, R. L. and Ogilvie, K. K.; J. Org. Chem. 32:296 (1967), or that of Kugel, C., Lellouche, J.-P., and Beaucourt, J.-P., Tetrahedron Lett. 30:4947 (1989).

To an anhydrous dichloromethane (200 mL) solution of 4-nitrophenyl chloroformate (9.02 g, 45 mmole) under nitrogen at 5° C. was added drop-wise a dichloromethane (100 mL) solution of 4-bromobenzyl alcohol (8.79 g, 47 mmole, 1.04 eq) and pyridine (7.3 mL, 90 mmole, 2 eq). After 1 hour, the reaction was allowed to warm to room temperature. After 2 hours, TLC with dichloromethane:hexane (4:1) showed no starting alcohol. The dichloromethane was washed with 1N HCl (3×100 mL), brine (2×150 mL), dried (MgSO$_4$), filtered, and evaporated in vacuo to give 15.7 g of a white solid. Triturated in ether/hexane, filtered and dried to give 13.29 g (84%) of product.

mp: 121–123° C.; $^1$H NMR (CDCl$_3$): δ5.24 (2H, s); 7.32 (2H, d, J=8 Hz); 7.37 (2H, d, J=9 Hz); 7.55 (2H, d, J=8 Hz); 8.27 (2H, d, J=9 Hz); MS: MW=352.14, observed (FD, MeOH) 351, 353; IR(CHCl$_3$): 1529, 1767; EA: Anal. Calcd for C$_{14}$H$_{10}$BrNO$_5$:C, 47.75; H, 2.86; N, 3.98. Found:C, 48.00; H, 2.97; N, 4.11.

Part B

To an anhydrous DMF suspension of 7-[2-(2-phenyl-4-oxazolyl)ethoxy]-1,2,3,4-tetrahydroisoquinoline 3-carboxylic acid under nitrogen is added 3 equivalents of cesium carbonate and after cooling to 5° C., one equivalent of 4-bromobenzyl 4-nitrophenylcarbonate.

Example 15
7-[2-(2-Phenyl-4-oxazolyl)ethoxy]-1,2,3,4-tetrahydro-N-(4-trifluoromethylbenzyl)oxycarbonyl-isoquinoline-3-carboxylic acid.

Part A. (4-Trifluoromethylbenzyl)-(4-nitrophenyl) Carbonate.

In a manner similar to Example 14, Part A, 4-nitrophenyl chloroformate (10.08 g, 50 mmole) was treated with 4-(trifluoromethyl)benzyl alcohol (7.2 mL, 52.5 mmole, 1.05 eq) and pyridine (8.1 mL, 100 mmole, 2 eq). Trituration in ether provided 11.87 g (70%) of a white solid.

mp: 95.5–96.5° C.; EA: Anal. Calcd for C$_{15}$H$_{10}$F$_3$NO$_5$:C, 52.80; H, 2.95; N, 4.11. Found:C, 52.94; H, 2.94; N, 4.20. $^1$H NMR (CDCl$_3$): δ5.35 (2H, s); 7.39 (2H, d, J=9 Hz); 7.57; (2H, d, J=8 Hz); 7.68 (2H, d, J=8 Hz); 8.28 (2H, d, J=9 Hz); MS: MW=341.24, observed (FD, MeOH) 341; IR(CHCl$_3$): 1530, 1768.

Part B

To an anhydrous DMF suspension of 7-[2-(2-phenyl-4-oxazolyl)ethoxy]-1,2,3,4-tetrahydroisoquinoline 3-carboxylic acid under nitrogen is added 3 equivalents of cesium carbonate and after cooling to 5° C., one equivalent of 4-trifluoromethylbenzyl-4-nitrophenylcarbonate.

Example 16
7-[2-(2-Phenyl-4-oxazolyl)ethoxy]-1,2,3,4-tetrahydro-N-(4-Methoxybenzyl)oxycarbonyl-isoquinoline-3-carboxylic acid.

Part A

In a manner similar to Example 17, Part A 4-nitrophenyl chloroformate (10.08 g, 50 mmole) was treated with 4-methoxybenzyl alcohol (6.6 mL, 52.5 mmole, 1.05 eq) and pyridine (8.1 mL, 100 mmole, 2 eq). Trituration in ether/hexane provided 13.83 g (91%) of a white solid.

mp: 106–107° C.; EA: Anal. Calcd for $C_{15}H_{13}NO_6$:C, 59.41; H, 4.32; N, 4.62. Found:C, 59.70; H, 4.42; N, 4.71. $^1$H NMR (CDCl$_3$): δ3.83 (3H, s); 5.24 (2H, s); 6.93 (2H, d, J=8.5 Hz); 7.37 (2H, d, J=9 Hz); 7.39 (2H, d, J=8.5 Hz); 8.27 (2H, d, J=9 Hz); MS: MW=303.27, observed (FD, MeOH) 303.

Part B

The procedure of Example 15, Part B is followed, substituting 4-methoxybenzyl-4-nitrophenylcarbonate for 4-trifluoromethylbenzyl-4-nitrophenylcarbonate.

Example 17

7-[2-(2-Phenyl-4-oxazolyl)ethoxy]-1,2,3,4-tetrahydro-N-(4-n-butylbenzyl)oxycarbonyl-isoquinoline-3-carboxylic acid.

Part A

In a manner similar to Example 14, Part A 4-nitrophenyl chloroformate (10.08 g, 50 mmole) was treated with 4-butylbenzyl alcohol (9 mL, 52.5 mmole, 1.05 eq) and pyridine (8.1 mL, 100 mmole, 2 eq). Evaporation in vacuo provided 15.57 g (95%) of a light yellow oil.

EA: Anal. Calcd for $C_{18}H_{19}NO_5$: C, 65.64; H, 5.82; N, 4.25. Found: C, 65.45; H, 5.62; N, 4.48. $^1$H NMR (CDCl$_3$): δ0.93 (3H, t, J=7 Hz); 1.38 (2H, m); 1.61 (2H, m); 2.64 (2H, J=8 Hz); 5.27 (2H, s); 7.22 (2H, d, J=8 Hz); 7.36 (2H, d, J=8 Hz); 7.38 (2H, d, J=9 Hz); 8.27 (2H, d, J=9 Hz); MS: MW=329.36, observed (FD, MeOH) 329; IR(CHCl$_3$): 1529, 1766, 2933, 2961.

Part B

The procedure of Example 15, Part B is followed, substituting 4-n-butylbenzyl-4-nitrophenylcarbonate for 4-trifluoromethylbenzyl-4-nitrophenylcarbonate.

Example 18

7-[2-(2-Phenyl-4-oxazolyl)ethoxy]-1,2,3,4-tetrahydro-N-(N'-Benzyl)-carbamoyl-isoquinoline-3-carboxylic acid.

The method described in Arrieta, A. and Palomo, C., Synthesis (1982) 1050 is followed. To a partial THF (100 mL) solution of 7-[2-(2-phenyl-4-oxazolyl)ethoxy]-1,2,3,4-tetrahydroisoquinoline 3-carboxylic acid under nitrogen is added one equivalent of 1,1,1,3,3,3-hexamethyldisilazane and stirred for 30 minutes. Then, one equivalent of benzyl-isocyanate is added and the mixture is stirred for 16 hours. The volume of THF is reduced in half and water/EtOAc (1:5, vol:vol) is added to precipitate the product.

Male obese-diabetic viable yellow (Avy) mice were divided into two groups of 6 each. One group was fed repelletized Purina 5008 Chow and the second group was fed a repelletized chow consisting of Purina 5008 Chow, admixed with varying doses of the candidate compound. Blood samples were taken before the experiment was initiated and 14 days after initiation. Body weight and food consumption were monitored. The blood glucose level after 14 days of treatment was measured and recorded as a percent of the initial value, compared to the untreated control (first) group. The results are presented in the table below and include the dose of the candidate compound as a weight percent of the amount incorporated into the diet. The positive control is a known hypoglycemic agent (*J. Med. Chem.* 35:2617, 1992) administered in the same way as a compound of the present invention.

TABLE 1

Serum glucose levels after 14 days of administration of a compound of the Formula I.

| Compound Administered | Dose (g/100 g food) | Serum Glucose after 14 days % of day 0 value |
| --- | --- | --- |
| Example No. 1 (positive control) | 0.03 0.003 | 32 29 |

In the same feeding study described above, plasma triglycerides were measured against a glycerol standard using reagents from Sigma Kit No. 339 (St. Louis, Mo.), adapted for assay on the Monarch System (Instrumentation Laboratory, Lexington, Mass.). Day 14 levels are recorded below as mM of triglycerides per mL. Serum triglyceride values for untreated animals averaged about 4 mmol/mL.

TABLE 2

Serum triglyceride levels after 14 days of administration of a compound of the Formula I.

| Compound Administered | Dose (g/100 g food) | Serum Triglyceride after 14 days (mmol/mL) |
| --- | --- | --- |
| Example No. 1 clofibric acid (positive control) | 0.03 0.10 | 2.5 1.9 |

We claim:
1. A 1,2,3,4-tetrahydroisoquinoline compound of Formula I:

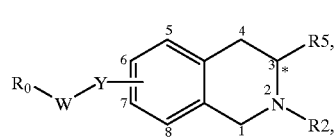

(I)

wherein:
R$^0$ is selected from the group consisting of

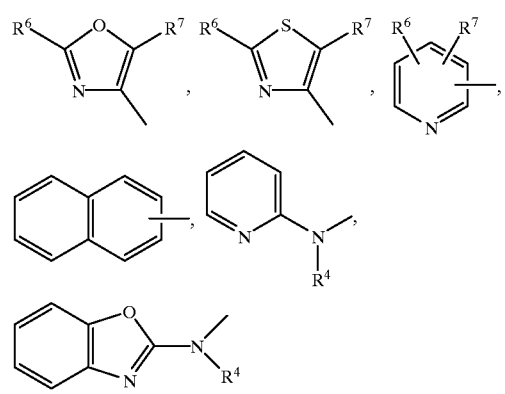

and

R$^2$ is hydrogen, C$_{1-4}$ acyl, C$_{1-4}$ alkyloxycarbonyl, C$_{1-4}$ alkylaminocarbonyl, arylcarbonyl, aryloxycarbonyl, aryloxy C$_{1-4}$ alkylcarbonyl, arylaminocarbonyl, aryl C$_{1-4}$ acyl, aryl C$_{1-4}$ alkyloxycarbonyl, aryl C$_{1-4}$ alkylaminocarbonyl, aryl C$_{1-4}$ alkylsulfonyl, or an amino-protecting group;

R⁴ is hydrogen, or $C_{1-4}$ alkyl;
R⁵ is —COOH, —CONR¹⁰R¹¹, —CN, —CONHOH, or

R⁶ is hydrogen, $C_{1-4}$ alkyl, aryl, or aryl $C_{1-4}$ alkyl;
R⁷ is hydrogen, halogen, or $C_{1-4}$ alkyl;
R⁹ is hydrogen, $C_{1-4}$ alkyl, or aryl;
R¹⁰ and R¹¹ are independently hydrogen, $C_{1-4}$ alkyl, or aryl;
W is —(CH₂)n—;
Y is attached at position 6 or at position 7 of the 1,2,3,4-tetrahydroisoquinoline moiety, and is —O—, —S—, —SO—, —SO₂—, —NH—, —CONR⁹—, —NR⁹—SO₂—, or —SO₂—NR⁹—; and
n is 1 to 4;
or a pharmaceutically-acceptable salt thereof.

2. The compound of claim 1, wherein:
R⁰ is or

R² is hydrogen, $C_{1-4}$ alkyloxycarbonyl, arylcarbonyl, aryloxycarbonyl, arylaminocarbonyl, aryl $C_{1-4}$ alkyloxycarbonyl, aryloxy $C_{1-4}$ alkylcarbonyl, aryl $C_{1-4}$ alkylsulfonyl, or an amino-protecting group;
R⁴ is hydrogen or methyl;
R⁵ is —COOH, —CONR⁹R¹⁰, or R⁶ is aryl;
R⁷ is hydrogen, halogen, or methyl;
R⁹ and R¹⁰ are hydrogen; and
Y is —O— or —S—,
or a pharmaceutically-acceptable salt thereof.

3. The compound of claim 2, wherein:

R⁰ is
R² is arylcarbonyl, aryloxycarbonyl, aryl $C_{1-4}$ alkyloxycarbonyl, aryl $C_{1-4}$ alkylsulfonyl, or an amino-protecting group;
R⁵ is —COOH;
Y is —O—; and
n is 1 or 2;
or a pharmaceutically-acceptable salt thereof.

4. The compound of claim 3, wherein:

R⁰ is
R² is hydrogen, benzyloxycarbonyl, phenylcarbonyl, benzylcarbonyl, methylbenzylcarbonyl, phenyloxycarbonyl, para-chlorophenylcarbonyl, benzylsulfonyl, para-bromophenyloxycarbonyl, para-trifluoromethylphenyloxycarbonyl, para-methoxyphenyloxycarbonyl, para-n-butylphenyloxycarbonyl, phenyloxymethylcarbonyl, benzylaminocarbonyl, or ethoxycarbonyl;
R⁶ is phenyl;
R⁷ is hydrogen;
Y is attached at the 7 position; and
n is 2;
or a pharmaceutically-acceptable salt thereof.

5. The compound of the formula:

or a pharmaceutically-acceptable salt thereof.

6. The compound of claim 1, wherein Y is attached at the 7 position of the 1,2,3,4-tetrahydroisoquinoline moiety.

7. The compound of claim 1, wherein Y is attached at the 6 position of the 1,2,3,4-tetrahydroisoquinoline moiety.

8. The compound of claim 1, which is the R enantiomer.

9. The compound of claim 1, which is the S enantiomer.

10. The compound of claim 1, which is the racemate.

11. A pharmaceutical formulation comprising as a active ingredient a compound of formula (I), as claimed in claim 1, together with one or more pharmaceutically-acceptable excipients.

12. A pharmaceutical formulation comprising the compound of claim 5, or a pharmaceutically-acceptable salt thereof, together with one or more pharmaceutically-acceptable excipients.

13. A method of treating hyperglycemia comprising administering to a mammal an effective dose of the compound of claim 1.

14. A method of treating hyperglycemia comprising administering to a mammal an effective dose of the compound of claim 5.

15. A method of treating hyperlipidemia comprising administering to a mammal an effective dose of the compound of claim 1.

16. A method of treating hyperlipidemia comprising administering to a mammal an effective dose of the compound of claim 5.

17. A process for preparing a 1,2,3,4-tetrahydroisoquinoline compound of Formula I:

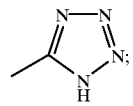

(I)

wherein:

$R^0$ is selected from the group consisting of

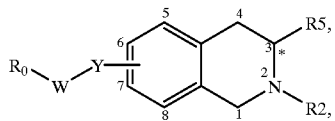

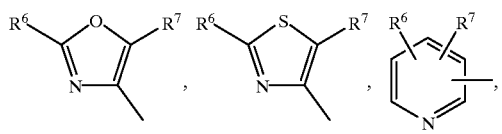

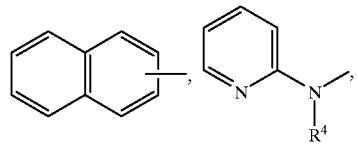

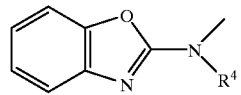

and $R^2$ is hydrogen, $C_{1-4}$ acyl, $C_{1-4}$ alkyloxycarbonyl, $C_{1-4}$ alkylaminocarbonyl, arylcarbonyl, aryloxycarbonyl, aryloxy $C_{1-4}$ alkylcarbonyl, arylaminocarbonyl, aryl $C_{1-4}$ acyl, aryl $C_{1-4}$ alkyloxycarbonyl, aryl $C_{1-4}$ alkylaminocarbonyl, aryl $C_{1-4}$ alkylsulfonyl, or an amino-protecting group;

$R^4$ is hydrogen, or $C_{1-4}$ alkyl;

$R^5$ is —COOH, —CONR$^{10}$R$^{11}$, —CN, —CONHOH, or

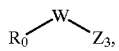

$R^6$ is hydrogen, $C_{1-4}$ alkyl, aryl, or aryl $C_{1-4}$ alkyl;

$R^7$ is hydrogen, halogen, or $C_{1-4}$ alkyl;

$R^9$ is hydrogen, $C_{1-4}$ alkyl, or aryl;

$R^{10}$ and $R^{11}$ are independently hydrogen, $C_{1-4}$ alkyl, or aryl;

W is —(CH$_2$)n—;

Y is attached at position 6 or at position 7 of the 1,2,3,4-tetrahydroisoquinoline moiety, and is —O—, —S—, —SO—, —SO$_2$—, —NH—, —CONR$^9$—, —NR$^9$—SO$_2$—, or —SO$_2$—NR$^9$—; and n is 1 to 4;

or a pharmaceutically-acceptable salt thereof, comprising:

A. A. reacting a compound of the formula

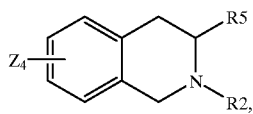

wherein Z3 is —OH, —SO$_2$Cl, a halogen leaving group, —NHR$^9$, or —COCl, with a compound of the formula

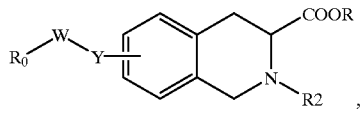

wherein Z4 is —OH, —SH, —NH$_2$, or —SO$_2$Cl, to form a compound of formula (I); or B. deprotecting a compound of the formula wherein R is a carboxy protecting group, to form a compound of formula (I) wherein $R^5$ is a free carboxy group.

* * * * *